United States Patent [19]
Edwards et al.

[11] Patent Number: 5,916,898
[45] Date of Patent: Jun. 29, 1999

[54] PHENANTHROLINE DERIVATIVES

[75] Inventors: Philip Neil Edwards, Stockport; Michael Stewart Large, Stoke-on-Trent; Neil James Hales, Macclesfield, all of United Kingdom

[73] Assignee: Zeneca Limited, London, United Kingdom

[21] Appl. No.: 08/957,450

[22] Filed: Oct. 24, 1997

[51] Int. Cl.$^6$ ...................... A61K 31/435; C07D 471/18
[52] U.S. Cl. ............................................. 514/292; 546/88
[58] Field of Search ................................ 546/88; 514/292

[56] References Cited

U.S. PATENT DOCUMENTS

| | | | |
|---|---|---|---|
| 3,951,833 | 4/1976 | Juda et al. | 252/51.5 R |
| 4,156,726 | 5/1979 | Brown et al. | 424/258 |
| 4,328,230 | 5/1982 | Brown et al. | 424/256 |
| 5,369,106 | 11/1994 | Nakamura et al. | 514/218 |
| 5,393,614 | 2/1995 | Nakada | 428/690 |
| 5,556,852 | 9/1996 | Nakamura et al. | 514/218 |
| 5,559,109 | 9/1996 | Nakamura et al. | 514/218 |

FOREIGN PATENT DOCUMENTS

| | | |
|---|---|---|
| 0 326 835 A1 | 8/1989 | European Pat. Off. . |
| 0 395 446 A2 | 10/1990 | European Pat. Off. . |
| 0 564 224 A2 | 10/1993 | European Pat. Off. . |
| 1 147 760 | 4/1969 | United Kingdom . |
| 1 335 623 | 10/1973 | United Kingdom . |
| 1 504 709 | 3/1978 | United Kingdom . |

OTHER PUBLICATIONS

Chemical Abstracts vol. 74 (69964n): p.438 (1971).
Chemical Abstracts vol. 79(105229r): p.428 (1973).
Chemical Abstracts vol. 79(105230j): p.428 (1973).
Chemical Abstracts vol. 81(120597u): p.536 (1974).
Chemical Abstracts vol. 81(120596t): p. 536 (1974).
Chemical Abstracts vol. 81(136130x): p. 424 (1974).
Chemical Abstracts vol. 95(132697d): p. 655 (1981).
J. Lee, et al., "Quinolone(II):Synthesis of Fluoro–substituted Pyrido[3, 2–h] quinolone Derivatives as Potential Antibacterials," *Korean J. of Med. Chem. vol.* 4(2): pp. 92–100 (1994).
D. Markees, "The Synthesis of Some 1,8–Phenanthrolines and Related Compounds," *Helvetica Chimica Acta vol.* 66(2)–Nr.55: pp. 620–626 (1983).
J. Lee, et al., "New Quinolones(I) Synthesis of New Pyrido [3,2–h] quinoline Derivatives and Their Antibacterial Activities," *Bull. Korean Chem. Soc. vol.* 13(5): pp. 571–573 (1992).
J. A. Shelnutt, "Metal Effects on Metalloporphyrins and on their π–π Charge–Transfer Complexes with Aromatic Acceptors: Urohemin Complexes," *Inorg. Chem. vol.* 22(18): pp. 2535–2544 (1983).
J. A. Shelnutt, "Molecular Complexes of Copper Uroporphyrin with Aromatic Acceptors," *J. Phys. Chem. vol.* 87(4): pp. 605–616 (1983).
J. A. Shelnutt, "Structure of Molecular Complexes of Copper Uroporphyrin with Aromatic Heterocycles," *J. Am. Chem. Soc. vol.* 103(14): pp. 4275–4277 (1981).
F. Chui, et al., "Synthesis of 4–Amino Substituted and 4–Unsubstituted 1,10–Phenanthroline–3–carboxylic Acid Derivatives as Potential DNA Cleavage Reagents," *Tetrahedron vol.* 50(3): pp. 889–894 (1994).
K. J. Liska, "Preparation and Antitumor Properties of Analogs of Acronycine," *J. of Medicinal Chemistry vol.* 15(11): pp. 1177–1179 (1972).
E. T. Nakhleh, et al., "Isoelectric Focusing of Phenanthroline Iron Complexes and Their Possible Use as pH Markers," *Analytical Biochemistry vol.* 49: pp. 218–224 (1972).
D. P. Poe, "Relationship between Reduction Potentials and Mixing Constants of Mixed–Ligand Complexes," *Inorg. Chem. vol.* 27(7): pp. 1280–1283 (1988).
D. P. Poe, et al., "Mixed–Ligand Complexes of Iron and Hydroxy–1,10–Phenanthrolines" *Talanta vol.* 27: pp. 1007–1012 (1980).
L. Gut, et al., "Porphyric Insecticides. IV: Structure–Activity Study of Substituted Phenanthrolines," *Pestic. Sci. vol.* 39: pp. 19–30 (1993).
D. P. Poe, et al., "Iron (III) Derivatives of 4,7–Dihydroxy–1, 10–Phenanthroline," *Talanta vol.* 23: pp. 141–145 (1976).
D. P. Poe, et al., "Spectrophotometric Determination of Iron in Highly Alkaline Solution with 4–Hydroxy–1,10–Phenanthroline," *Talanta vol.* 27: pp. 368–370 (1970).
D. P. Poe, "The Spectrophotometric Determination of Dissolved Oxygen and Other Uses of 4.7–Dihydroxy–1, 10–Phenanthroline," *Diss. Abstr. Int.B* 35(11): p. 5274 (1975).

*Primary Examiner*—Joseph K. McKane
*Attorney, Agent, or Firm*—Pillsbury Madison & Sutro LLP

[57] ABSTRACT

The present invention provides a phenanthroline derivative of formula (I)

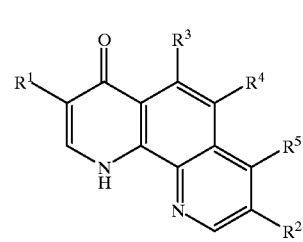

(I)

wherein, for example, R$^1$ is hydrogen, carboxy, cyano, nitro, (1–4C)alkyl, (1–6C)alkoxycarbonyl, (1–4C)alkylamino, (2–4C)alkanoyl, (1–4C)alkoxy-(2–4C)alkoxy-(2–4C) alkoxycarbonyl or N-[amino-(2–8C)alkyl]carbamoyl;

R$^2$ is, for example, hydrogen, carboxy, (1–6C) alkoxycarbonyl, carbamoyl, N-(1–8C)alkylcarbamoyl, N,N-di-(1–8C)alkylcarbamoyl, N-(1–4C) alkylcyclohexylcarbamoyl, 1,2,3,4-tetrahydro-isoquinolin-2-ylcarbonyl or N,N-[di-(1–4C)alkyl] thiocarbamoyl;

R$^3$ and R$^4$, which may be the same or different, are, for example, hydrogen or halo; and R$^5$ is, for example, hydrogen, di-(1–4C)alkylamino or halo; or a pharmaceutically-acceptable salt thereof.

The invention further provides pharmaceutical compositions comprising phenanthroline derivatives, processes for making the same and their use in producing an anti-fibroproliferative effect.

31 Claims, No Drawings

PHENANTHROLINE DERIVATIVES

The present invention relates to phenanthroline derivatives which inhibit the enzyme prolyl 4-hydroxylase, processes for preparing these compounds and pharmaceutical compositions thereof. The present invention also relates to the therapeutical use of such compounds.

BACKGROUND OF THE INVENTION

There are many disorders known wherein the proliferation of fibrotic tissue is a characteristic feature. Examples of such disorders include, for example, rheumatoid arthritis, chronic arthritis, osteoarthritis, hepatic fibrosis, hepatic cirrhosis, pulmonary fibrosis, renal fibrosis, cardiac fibrosis, arteriosclerosis tumour-associated fibrosis and the formation of scar tissue following injury or surgery. Thus, a therapeutic agent which possesses anti-fibrotic properties may be of value in the treatment of one or more of these disorders.

It is known that the enzyme prolyl 4-hydroxylase is involved in the hydroxylation of proline residues in collagenous protein, and that 4-hydroxyproline residues are essential for the formation of the characteristic triple helical form of collagen which is secreted into fibrotic tissue. Consequently, a compound which inhibits the activity of prolyl 4-hydroxylase may be of potential value in the treatment of fibroproliferative disease, which is characterized by excessive collagen production.

Various chemical compounds have been reported to inhibit prolyl 4-hydroxylase; for example, 2,2'-dipyridyl (W. Muller et al., *FEBS Letters,* 90:218 (1978)), pyridine-2,4-dicarboxylic acid (K. Majamaa et al., *Eur.J.Biochem.,* 138:239 (1984)), pyridine-2,4-dicarboxlic acid derivatives and pyridine-2,5-dicarboxylic acid deivatives (European Patent Application Nos. 278452, 278453, 278454 and 281943) and heterocyclic carbonylglycines (T. J. Franklin et al., *Biochem. Soc. Trans.,* 19:812–815 (1991)).

Despite previous efforts, a need exists for safe and effective means for the treatment of fibroproliferative diseases and disorders.

SUMMARY OF THE INVENTION

The present invention provides certain phenanthroline derivatives useful for inhibiting prolyl 4-hydroxylase.

Specifically, the present invention provides phenanthroline derivatives of formula (I)

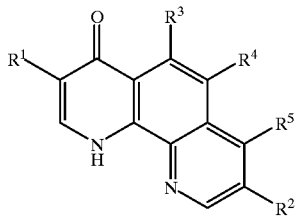

(I)

wherein $R^1$ is hydrogen, carboxy or an ester derivative thereof, cyano, halo, nitro, amino, (1–4C)alkyl, (1–4C)alkylamino, di-(1–4C)alkylamino, (1–6C)alkoxycarbonyl, (2–4C)alkanoy, hydroxy-(1–4C)alkyl, carbamoyl, N-(1–4C)alkylcarbamoyl, (1–4C)alkylthio, (1–4C)alkylsulfinyl, (1–C)alkylsulfonyl, phenylthio, phenylsulfinyl, phenylsulfonyl, fluoro-(1–4C)alkylthio, fluoro-(1–4C)alkylsulfinyl, fluoro-(1–4C)alkylsulfonyl, (1–4C)alkoxy-(2–4C)alkoxycarbonyl, N,N-di-[(1–4C)alkyl]carbamoyl-(1–4C)alkoxycarbonyl, (1–4C)alkylamino-(2–4C)alkoxycarbonyl, di-(1–4C)alkylamino-(2–4C)alkoxycarbonyl, (1–4C)alkoxy-(2–4C)alkoxy-(2–4C)alkoxycarbonyl, (2–4C)alkanoyloxy-(1–4C)alkyl or N-[amino-(2–8C)alkyl]carbamoyl;

$R^2$ is hydrogen, hydroxy, amino, cyano, halo, (1–4C)alkyl, carboxy or an ester derivative thereof, (1–4C)alkylamino, di-(1–4C)alkylamino, (1–6C)alkoxycarbonyl, (2–4C)alkanoyl, (1–4C)alkoxy, carboxy-(1–4C)alkoxy, (1–4C)alkoxycarbonyl-(1–4C)alkoxy, carbamoyl, N-(1–8C)alkylcarbamoyl, N,N-di-(1–8C)alkylcarbamoyl, N-[amino-(2–8C)alkyl)carbamoyl, N-[(1–4C)alkylamino-(1–8C)alkyl]carbamoyl, N[di-(1–4C)alkylamino-(1–8C)alkyl]carbamoyl, N-cyclohexylcarbamoyl, N-[cyclopentyl]carbamoyl, N-phenylcarbamoyl, N-(1–4C)alkylcyclohexylcarbamoyl, N-(1–4C)alkylcyclopentylcarbamoyl, N-(1–4C)alkyl-N-phenylcarbamoyl, N,N-diphenylcarbamoyl, N-[phenyl-(1–4C)alkyl]carbamoyl, N-(1–4C)alkyl-N-[phenyl-(1–4C)alkyl)carbamoyl, N,N-di-[phenyl-(1–4C)alkyl)carbamoyl, N-[(2–4C)alkanoyl]carbamoyl, N-[(1–4C)alkoxycarbonyl]carbamoyl, N-[fluoro-(2–6C)alkylcarbamoyl, N-[fluoro-(2–6C)alkyl]-N-(1–4C)alkylcarbamoyl, N,N-[di-fluoro-(2–6C)alkyl]carbamoyl, pyrrolidin-1-ylcarbonyl, piperidinocarbonyl, piperazin-1-ylcarbonyl, morpholinocarbonyl, 1,2,3,4-tetrahydro-isoquinolin-2-ylcarbonyl, N,N-[di-(1–4C)alkyl]thiocarbamoyl, N-(2–4C)alkanoylamino or N-[(1–4)alkoxycarbonyl]amino;

$R^3$ and $R^4$, which may be the same or different, are hydrogen, (1–4C)alkyl, (2–4C)alkoxy, halo, nitro, hydroxy, fluoro-(1–4C)alkyl or pyridinyl;

or $R^4$ is methoxy; and $R^5$ is hydrogen, hydroxy, amino, (1–4C)alkylamino, di-(1–4C)alkylamino, halo, (1–4C)alkoxy-(2–4C)alkoxy, fluoro-(1–6C)alkoxy, pyrrolidin-1-yl, piperidino, piperazin-1-yl or morpholino;

or a pharmaceutically-acceptable salt thereof.

It will be understood that the phenyl groups in the afore-mentioned substituents are optionally substituted with one to four substituents selected from halo, (1–4C)alkoxy, (1–4C)alkyl, cyano, hydroxy and trifluoromethyl. It will also be understood that the heterocyclic groups pyrrolidin-1-yl, piperidino, piperazin-1-yl and morpholino in the afore-mentioned substituents are optionally substituted in any vacant position with one to four substituents selected from (1–4C)alkyl and benzyl.

As used herein, the "ester derivatives" preferably includes metabolically labile ester derivatives.

As used herein, the term "alkyl" includes both straight and branched chain groups. However, reference to individual groups such as propyl are specific for the straight chain version only. The term "(1–4C)alkyl" includes, for example, methyl, ethyl, propyl, isopropyl, butyl, isobutyl, sec-butyl and tert-butyl.

As used herein, the term "halo" includes, for example, fluoro, chloro, bromo and iodo.

The term (1–4C)alkylamino includes methylamino, ethylamino and propyl amino.

The term di-[(1–4C)alkyl]amino includes dimethylamino, N-ethyl-N-methyl amino, diethylamino, N-methyl-N-propylamino and dipropyl amino.

The term (2–4C)alkanoyl includes acetyl, propionyl and butyryl.

The term (1–6C)alkoxycarbonyl includes methoxycarbonyl, ethoxycarbonyl, propoxycarbonyl, tert-butoxycarbonyl and pentoxycarbonyl.

The term N-[amino-(2–8C)alkyl]carbamoyl includes N-(3-aminopropyl)carbamoyl, N-(6-aminohexyl)carbamoyl and N-(8-aminooctyl)carbamoyl.

The term (2–4C)alkoxy includes ethoxy, propoxy, isopropoxy, butoxy, isobutoxy, sec-butoxy and tert-butoxy.

The term hydroxy-(1–4C)alkyl includes hydroxymethyl, 1-hydroxyethyl, 2-hydroxyethyl and 3-hydroxypropyl.

The term (1–4C)alkylthio includes methylthio, ethylthio and propylthio.

The term (1–4C)alkylsulfinyl includes methylsulfinyl, ethylsulfinyl and propylsulfinyl.

The term (1–4C)alkylsulfonyl includes methylsulfonyl, ethylsulfonyl and propylsulfonyl.

The term fluoro-(1–4C)alkylthio includes trifluoromethylthio, 2,2,2-trifluoroethylthio and 3,3,3-trifluoropropylthio.

The term fluoro-(1–4C)alkylsulfinyl includes trifluoromethylsulfinyl, 2,2,2-trifluoroethylsulfinyl and 3,3,3-trifluoropropylsulfinyl.

The term fluoro-(1–4C)alkylsulfonyl includes trifluoromethylsulfonyl, 2,2,2-trifluoroethylsulfonyl and 3,3,3-trifluoropylsulfinyl.

The term (1–4C)alkoxy-(2–4C)alkoxycarbonyl includes 2-methoxyethoxycarbonyl, 2-ethoxyethoxycarbonyl and 3-methoxypropoxycarbonyl.

The term N-(1–4C)alkylcarbamoyl includes N-methylcarbamoyl, N-ethylcarbamoyl and N-butylcarbamoyl.

The term N,N-di-[(1–4C)alkyl]carbamoyl-(1–4C)alkoxycarbonyl includes N,N-dimethylcarbamoylmethoxycarbonyl, N,N-diethylcarbamoylmethoxycarbonyl, 2-(N,N-dimethylcarbamoyl)-ethoxycarbonyl, 2-(N,N-diethylcarbamoyl)-ethoxycarbonyl and 3-(N,N-dimethylcarbamoyl)-propoxycarbonyl.

The term (1–4C)alkylamino-(2–4C)alkoxycarbonyl includes 2-(methylamino) ethoxycarbonyl, 2-(ethylamino) ethoxycarbonyl and 3-(methylamino)propylcarbonyl.

The term di-(1–4C)alkylamino-(2–4C)alkoxycarbonyl includes 2-(dimethylamino)ethoxycarbonyl, 2-(diethylamino)ethoxycarbonyl, 2-(N-ethyl N-methylamino)ethoxycarbonyl and 3-(dimethylamino) propoxycarbonyl.

The term (1–4C)alkoxy-(2–4C)alkoxy-(2–4C)alkoxycarbonyl includes 2-(2-methoxyethoxy) ethoxycarbonyl, 2-(2-ethoxyethoxy)ethoxycarbonyl and 3-(2-methoxyethoxy)propoxycarbonyl.

The term (2–4)alkanoyloxy-(1–4C)alkyl includes acetoxymethyl, propionyloxymethyl, butyryloxymethyl, 2-acetoxyethyl and 3-acetoxypropyl.

The term (1–4C)alkoxy includes methoxy, ethoxy, propoxy, isopropoxy, butoxy, isobutoxy, sec-butoxy and tert-butoxy.

The term carboxy-(1–4C)alkoxy includes carboxymethoxy, 2-carboxyethoxy and 3-carboxypropoxy.

The term (1–4C)alkoxycarbonyl-(1–4C)alkoxy includes methoxycarbonylmethoxy, 2-(methoxycarbonyl)ethoxy and 2-(ethoxycarbonyl)ethoxy.

The term N-(1–8C)alkylcarbamnoyl includes N-methylcarbamoyl, N-ethylcarbamoyl, N-butylcarbamoyl, N-hexylcarbamoyl and N-octylcarbamoyl.

The term N,N-di-(1–8C)alkylcarbamoyl includes N,N-dimethylcarbamoyl, N, N-diethylcarbamoyl, N, N-di-sec-butylcarbamoyl, N, N-dibutylcarbamoyl, N-methyl-N-butylcarbamoyl, N-methyl-N-hexylcarbamoyl, N-methyl-N-ethyl carbamoyl, N-ethyl-N-butylcarbamoyl, N-ethyl-N-pentylcarbamoyl, N-ethyl-N-propylcarbamoyl and N-ethyl-N-isopropylcarbamoyl.

The term N-(1–4C)alkylamino-(1–8C)alkyl]carbamoyl includes N-[methylaminomethyl]carbamoyl, N-[ethylaminomethyl]carbamoyl, N-[2-methylaminoethyl]carbamoyl, N-[3-methylaminopropyl]carbamoyl, N-[6-methylaminohexyl]carbamoyl and N-[8-methylaminooctyl]carbamoyl.

The term N-[di-(1–4C)alkylamino(1–8C)alkyl]carbamoyl includes N-[dimethylaminomethyl]carbamoyl, N-[diethylaminomethyl]carbamoyl, N-[N-methyl-N-ethylaminomethyl]carbamoyl, N-[2-dimethylaminoethyl]carbamoyl, N-[6-dimethylaminohexyl]carbamoyl and N-[8-dimethylaminooctyl]carbamoyl.

The term N-(1–4C)alkyl-N-cyclohexylcarbamoyl includes N-methyl-N-cyclohexylcarbamoyl, N-ethyl-N-cyclohexylcarbamoyl and N-propyl-N-cyclohexylcarbamoyl.

The term N-(1–4C)alkyl-N-cyclopentylcarbamoyl includes N-methyl-N-cyclopentylcarbamoyl, N-ethyl-N-cyclopentylcarbamoyl and N-propyl-N-cyclopentylcarbamoyl.

The term N-(1–4C)alkyl-N-phenylcarbamoyl incudes N-methyl-N-phenylcarbamoyl, N-ethyl-N-phenylcarbamoyl and N-propyl-N-phenylcarbamoyl.

The term N-[phenyl-(1–4C)alkyl]carbamoyl includes N-benzylcarbamoyl, N-(2-phenylethyl)carbamoyl and N-(3-phenylpropyl)carbamoyl.

The term N-(1–4C)alkyl-N-[phenyl(1–4C)alkyl]carbamoyl includes N-methyl-N-benzylcarbamoyl, N-ethyl-N-benzylcarbamoyl, N-isopropyl-N-benzylcarbamoyl, N-methyl-N-(2-phenylethyl)carbamoyl, N-ethyl-N-(2-phenylethyl)carbamoyl and N-methyl-N-(3-phenylpropyl)carbamoyl.

The term N,N-di-[phenyl-(1–4)alkyl]carbamoyl includes N,N-dibenzylcarbamoyl, N,N-di-(2-phenylethyl)carbamoyl and N,N-di-(3-phenylpropyl)carbamoyl.

The term N-[(2–4C)alkanoyl]carbamoyl includes N-acetylcarbamoyl, N-propionylcarbamoyl and N-butyrylcarbamoyl.

The term N-(1–4C)alkoxycarbonyl]carbamoyl includes N-methoxycarbonylcarbamoyl, N-ethoxycarbonylcarbamoyl and N-propoxycarbonylcarbamoyl.

The term N-[fluoro-(2–6C)alkyl]carbamoyl includes N-[2,2,2-trifluoroethyl]carbamoyl, N-[2,2,3,3,4,4,4-heptafluorobutyl]carbamoyl and N-[4,4,5,5,5-pentafluoropentyl]carbamoyl.

The term N-[fluoro-(2–6C)alkyl]-N-(1–4C)alkylcarbamoyl includes N-[2,2,2- trifluoroethyl]-N-ethylcarbamoyl, N-[2,2,3,3,4,4,4-heptafluorobutyl]-N-methylcarbamoyl and N-[4,4,5,5,5-pentafluoropentyl]-N-methylcarbamoyl.

The term N,N-[di-fluoro-(2–6C)alkyl]carbamoyl includes N,N-di-[2,2,3,3,4,4,4-heptafluorobutyl]carbamoyl and N,N-di-[4,4,5,5,5-pentafluoropentyl]carbamoyl.

The term N,N-[di-(1–4C)alkyl]thiocarbamoyl includes N,N-dimethylthiocarbamoyl, N,N-diethylthiocarbamoyl and N-methyl-N-ethylthiocarbamoyl.

The term N-(2–4C)alkanoylamino includes N-acetylamino-N-propionylamino and N-butyrylamino.

The term N-[(1–4C)alkoxycarbonyl]amino includes N-methoxycarbonylamino, N-ethoxycarbonylamino, N-propoxycarbonylamino and N-tert-butoxycarbonylamino.

The term fluoro-(1–4C)alkyl includes trifluoromethyl, 2,2,2-trifluoroethyl and 2,2,3,3,4,4,4-heptafluorobutyl.

The term pyridinyl includes pyridin-3-yl and pyridin-4-yl.

The term (1–4C)alkoxy-(2–4C)alkoxy includes 2-methoxyethoxy, 2-ethoxyethoxy and 3-methoxypropoxy.

The term fluoro-(1–6C)alkoxy includes 2,2,2-trifluoroethoxy, 4,4,5,5,5-pentafluoropentoxy and 2,2,3,3,4,4-heptafluorobutoxy.

Particular novel compounds of the invention include, for example, phenanthroline derivatives of the formula (I), or pharmaceutically-acceptable salts thereof, or a metabolically labile ester derivative of substituents $R^1$ and $R^2$ when either, or both, is a carboxy group, as defined in paragraphs (a) to (m) wherein, wherein, unless otherwise stated, each of $R^1$, $R^2$, $R^3$, $R^4$ and $R^5$ have any of the meanings defined hereinbefore or in this section concerning particular compounds of the invention:

(a) $R^1$ is hydrogen, carboxy, cyano, nitro, amino, (1–4C)alkyl, (1–4C)alkylamino, di-(1–4C)alkylamino, (1–6C)alkoxycarbonyl, (1–4C)alkylthio, (1–4C)alkylsulfinyl, (1–4C)alkylsulfonyl, phenylthio, phenylsulfinyl, phenylsulfonyl, fluoro-(1–4C)alkylsulfinyl, fluoro-(1–4C)alkylsulfonyl, (1–4C)alkoxy-(2–4C)alkoxycarbonyl, N-di-[(1–4C)alkyl]carbamoyl-(1–4C)alkoxycarbonyl, (1–4C)alkylamino-(2–4C)alkoxycarbonyl, di-(1–4C)alkylamino-(2–4C)alkoxycarbonyl, (1–4C)alkoxy-(2–4C)alkoxy-(2–4C)alkoxycarbonyl, 2–4C)alkanoyloxy-(1–4C)alkyl or N-[amino-(2–8C)alkyl]carbamoyl;

(b) $R^1$ is hydrogen, carboxy, cyano, halo, nitro, amino, (1–6C)alkoxycarbonyl, (2–4)alkanoyl, hydroxy-(1–4C)alkyl, (1–4C)alkylsulfonyl, phenylsulfonyl, N-[amino-(2–8C)alkyl]carbamoyl, fluoro-(1–4C)alkylsulfonyl, (1–4C)alkoxy-(2–4C)alkoxycarbonyl, N,N-di-[(1–4C)alkyl]carbamoyl-(1–4C)alkoxycarbonyl, (1–4C)alkoxy-(2–4C)alkoxy-(2–4C)alkoxycarbonyl or (2–4)alkanoyloxy-(1–4C)alkyl;

(c) $R^1$ is carboxy, cyano, nitro, (1–6C)alkoxycarbonyl, (2–4C)alkanoyl, fluoro-(1–4C)alkylsulfonyl or (1–4C)alkoxy-(2–4C)alkoxy-(2–4C)alkoxycarbonyl;

(d) $R^2$ is hydrogen, hydroxy, amino, cyano, carboxy, (1–6C)alkoxycarbonyl, (2–4C)alkanoyl, (1–4C)alkoxy, carboxy-(1–4C)alkoxy, carbamoyl, N-[amino-(2–8C)alkyl]-carbamoyl, N,N-di-(1–8C)alkylcarbamoyl, N-(1–4C)alkyl-N-cyclohexylcarbamoyl, N-phenylcarbamoyl, N-(1–4C)alkyl-N-phenylcarabamoyl, N-[phenyl-(1–4C)alkyl]carbamoyl, N-(1–4C)alkyl-N-[phenyl-(1–4C)alkyl]carbamoyl, N,N-di-[phenyl-(1–4C)alkyl]carbamoyl, N,-[(2–4C)alkanoyl]carbamoyl, N-[fluoro-(2–6C)alkyl]carbamoyl, N-[fluoro-(2 –6C)alkyl)-N-(1–4C)alkylcarbamoyl, pyrrolidin-1-ylcarbonyl, piperidinocarbonyl, piperazin-1-ylcarbonyl, 1,2,3,4-tetrahydroisoquinolin-2-ylcarbonyl, N-(2–4C)alkanoylamino, N-[di-(1–4C)alkoxycarbonyl]amino or N,N-[di-(1–4C)alkyl]thiocarbamoyl;

(e) $R^2$ is hydrogen, carboxy, (1–6C)alkoxycarbonyl, carbamoyl, N,N-di-(1–8C)alkylcarbamoyl, N-phenylcarbamoyl, N-(1–4C)alkyl-N-[phenyl-(1–4C)alkyl]carbamoyl, N-[fluoro-(2–6C)alkyl)carbamoyl, 1,2,3,4-tetrahydro-isoquinolin-2-ylcarbonyl, piperazin-1-ylcarbonyl or N,N-[di-(1–4C)alkyl]thiocarbamoyl;

(f) $R^2$ is hydrogen, hydroxy, carboxy, carboxy-(1–4C)alkoxy, carbamoyl, N-(1–8C)alkylcarbamoyl, N,N-di-(1–8C)alkylcarbamoyl, N-[amino-(2–8C)alkyl)carbamoyl, N-[(1–4C)alkylamino-(1–8C)alkyl)carbamoyl, N-[di-(1–4C)alkylamino-(1–8C)alkyl)carbamoyl, N-[(2–4C)alkanoyl]carbamoyl, piperazin-1-ylcarbonyl, morpholinocarbonyl, N-(2 –4C)alkanoylamino or N-[(1–4C)alkoxycarbonyl]amino;

(g) $R^3$ and $R^4$, which may be the same or different, are hydrogen, (1–4C)alkyl, halo, pyridinyl, fluoro-(1–4C)alkyl, nitro or hydroxy;

(h) $R^3$ and $R^4$, which may be the same or different, are hydrogen, (1–4C)alkyl, halo or pyridinyl;

(i) $R^3$ and $R^4$, which may be the same or different, are hydrogen, halo or nitro;

(j) $R^3$ is hydroxy;

(k) $R^5$ is hydrogen, hydroxy, pyrrolidin-1-yl, di-(1–4C)alkylamino, (1–4C)alkylamino, halo, (1–4C)alkoxy-(2–4C)alkoxy or fluoro-(1–6C)alkoxy;

(l) $R^5$ is hydrogen, di-(1–4C)alkylamino or halo; and (m) $R^5$ is hydrogen, hydroxy or piperazin-1-yl;

The phenyl groups in the afore-mentioned substituents in paragraphs (a), (b), (d) and (e) above are optionally substituted with one or two substituents selected from (1–4C)alkoxy, halo, hydroxy and trifluoromethyl; and the pyrrolidin-1-yl, piperidino and piperazin-1-yl groups in the aforementioned substituents in paragraphs (d), (e), (f) and (k) above are optionally substituted with one or two substituents selected from (1–4C)alkyl and benzyl.

It will be understood that the following compounds are excluded from the scope of compounds of formula (I): 3-carboxy-5,6-dihydroxy-4-oxo-3,4-dihydro-1,10-phenanthroline; 3-ethoxycarbonyl-4-oxo-3,4-dihydro-1,10-phenanthroline; 3,8-diethoxycarbonyl-7-hydroxy-4-oxo-3,4-dihydro-1,10-phenanthroline; 3,8-dicarboxy-7-hydroxy-4-oxo-3,4-dihydro-1,10-phenanthroline; 3,8-dicarboxy-7-hydroxy-5-methyl-4-oxo-3,4-dihydro-1,10-phenanthroline; 3,8-dicarbonyl-7-hydroxy-5-methyl-4-oxo-3,4-dihydro-1,10-phenanthroline; 5-butyl-3,8-dimethoxycarbonyl-7-hydroxy-4-oxo-3,4-dihydro-1,10-phenanthroline; 3-ethoxycarbonyl-6-fluoro-4-oxo-3,4-dihydro-1,10-phenanthroline; 7-hydroxy-4-oxo-3,4-dihydro-1,10-phenanthroline; 7-hdyroxy-4-oxo-3,4-dihydro-1,10-phenanthroline hydrochloride; 4-oxo-3,4-dihydro-1,10-phenanthroline; 7-dimethylamino-4-oxo-3,4-dihydro-1,10-phenanthroline; 3-carboxy-4-oxo-3,4-dihydro-1,10-phenanthroline; 3-carboxy-5-methyl-4-oxo-3,4-dihydro-1,10-phenanthroline and 5-hydroxy-4-oxo-3,4-dihydro-1,10-phenanthroline.

A preferred compound of the invention comprises a phenanthroline derivative of the formula (I), or a pharmaceutically-acceptable salt thereof, or a metabolically labile ester derivative of substituents $R^1$ and $R^2$ when either, or both, is a carboxy group, wherein $R^1$ is hydrogen, carboxy, cyano, nitro, amino, bromo, methoxycarbonyl, ethoxycarbonyl, acetyl, 2,2,2-trifluoroethylsulfonyl, 2-[2-methoxyethoxy]ethoxycarbonyl,1-hydroxyethyl, carbamoyl, methylsulfonyl, phenylsulfonyl, N-(6-aminohexyl)carbamoyl,2-methoxyethoxycarbonyl, N,N-diethylcarbamoylmethoxycarbonyl or propionyloxymethyl;

$R^2$ is hydroxy, amino, cyano, carboxy, methoxycarbonyl, ethoxycarbonyl, acetyl, carbamoyl, methoxy, carboxymethoxy, N-(6-aminohexyl)carbamoyl, N-ethyl-N-butylcarbamoyl, N,Ndiethylcarbamoyl, N-Ndisec-butylcarbamoyl, N-methyl-N-butylcarbamoyl, N-methyl-N-hexylcarbamoyl, N-ethyl-N-propylcarbamoyl, N-ethyl-N-isopropylcarbamoyl, N-ethyl-_-pentylcarbamoyl, N-ethyl-N-cyclohexylcarbamoyl, N-phenylcarbamoyl, N-methyl-N-phenylcarbamoyl, N-(2-phenylethyl)carbamoyl, N-methyl-N-benzylcarbamoyl, N-methyl-N-(2-phenylethyl)carbamoyl, N-isopropyl-N-benzylcarbamoyl, N-ethyl-N-benzylcarbamoyl, N,N-dibenzylcarbamoyl, N-[2,2,3,3,4,4,4-heptafluorobutyl]carbamoyl, N-[2,2,3,3,4,4,4-heptafluorobutyl]-N-methylcarbamoyl, N-[4,4,5,5,5- pentafluoropentyl]-N-methylcarbamoyl, 1,2,3,4-tetrahydro-isoquinolin-2-ylcarbonyl, pyrrolidin-1-ylcarbonyl, piperidinocarbonyl, piperazin-1-ylcarbonyl, N,N-diethylthiocarbamoyl, N-acetylamino or N-tert-butoxycarbonylamino;

R³ and R⁴, which may be the same or different, are hydrogen, fluoro, chloro, bromo, nitro, hydroxy, pyridin-4-yl, trifluoromethyl or methyl; and R⁵ is hydrogen, dimethylamino, diethylamino, chloro, bromo, hydroxy, pyrrolidin-1-yl, methylamino, 2-methoxyethoxy, 2,2,2-trifluoroethoxy or 4,4,5,5,5-pentafluoropentoxy;

wherein any phenyl group contained in the afore-mentioned R¹ and R² substituents are optionally substituted with one or two substituents selected from ethoxy, fluoro and trifluoromethyl; and any pyrrolidin-1-yl,piperidino or piperazin-1-yl group contained in the afore-mentioned R² substituents are optionally substituted with one methyl or benzyl substituent in any vacant position.

A further preferred compound of the invention comprises a phenanthroline derivative of the formula (I), or a pharmaceutically-acceptable salt thereof, or a metabolically labile ester derivative of substituents R¹ and R² when either, or both, is a carboxy group, wherein R¹ is hydrogen, carboxy, cyano, nitro, methyl, ethyl, methoxycarbonyl, ethoxycarbonyl, methylamino, ethylamino, dimethylamino, 2,2,2-trifluoroethylsulfonyl, 2,2,2-trifluoroethylsulfinyl, phenylsulfinyl, phenylsulfonyl, phenylthio, methylthio, methylsulfinyl, methylsulfonyl, 2-[2-methoxyethoxy]ethoxycarbonyl, N-(6-aminohexyl) carbamoyl, 2-methoxyethoxycarbonyl, 2-(methylamino) ethoxycarbonyl, 2-(dimethylamino)ethoxycarbonyl, N,N-diethylcarbamoylmethoxycarbonyl or propionyloxymethyl;

R² is hydrogen, hydroxy, carboxy, carbamoyl, carboxymethoxy, N-(6-aminohexyl) carbamoyl, N-ethylcarbamoyl, N-ethyl-N-butylcarbamoyl, N-butylcarbamoyl, N,N-diethylcarbamoyl, N,N-di-sec-butylcarbamoyl, N-methyl-N-butylcarbamoyl, N-methyl-N-hexylcarbamoyl, N-ethyl-N-propylcarbamoyl, N-ethyl-N-isopropylcarbaamoyl, N-ethyl-N-pentylcarbamoyl, piperazin-1-ylcarbonyl, N-[methylaminomethyl]carbamoyl, N-[dimethylaminomethyl]carbamoyl, N-acetylcarbamoyl, morpholinocarbonyl, N-acetylamino or N-tert-butoxycarbonylamino;

R³ and R⁴, which may be the same or different, are hydrogen, fluoro, chloro, bromo, methyl or pyridin-4-yl; or R³ is hydroxy; and R⁵ is hydrogen, hydroxy or piperazin-1-yl;

wherein any phenyl group contained in the afore-mentioned R¹ and R² substituents are optionally substituted with one or two substituents selected from ethoxy, fluoro and trifluoromethyl; and any piperazin-1-yl group contained in the afore-mentioned R² substituents is optionally substituted with one methyl or benzyl substituent in any vacant position.

A further preferred compound of the invention comprises a phenanthroline derivative of the formula (I), or a pharmaceutically-acceptable salt thereof, or a metabolically labile ester derivative of substituents R¹ and R² when either, or both, is a carboxy group, wherein R¹ is carboxy, cyano, nitro, ethoxycarbonyl, acetyl, 2,2, 2-trifluoroethylsulfonyl or 2-[2-methoxyethoxy] ethoxycarbonyl;

R² is hydrogen, carboxy, ethoxycarbonyl, carbamoyl, N-ethyl-N-butylcarbamoyl, N-(4-ethoxyphenyl)carbamoyl, N-methyl-N-benzylcarbamoyl, N-methyl-N-4-fluorobenzylcarbamo N-[2,2,3,3,4,4,4-heptafluorobutyl] carbamoyl, 1,2,3,4-tetrahydroisoquinolin-2-ylcarbonyl, 4-benzylpiperazin-1-ylcarbonyl or N,N-diethylthiocarbamoyl;

R³ and R⁴, which may be the same or different, are hydrogen, fluoro or nitro; and R⁵ is hydrogen, dimethylamino or chloro.

Further preferred compounds of the invention include, for example, the following phenanthroline derivatives of the formula (I):

3,8-dicarboxy-4-oxo-3,4-dihydro-1,10-phenanthroline;
8-carboxy-4-oxo-3,4-dihydro-1,10-phenanthroline;
3-nitro-4-oxo-3,4-dihydro-1,10-phenanthroline;
3-cyano-4-oxo-3,4-dihydro-1,10-phenanthroline;
3-cyano-5-hydroxy-4-oxo-3,4-dihydro-1,10-phenanthroline;
5-chloro-3-cyano-4-oxo-3,4-dihydro-1,10-phenanthroline;
5-chloro-3-ethoxycarbony-1-4-oxo-3,4-dihydro-1,10-phenanthroline;
5-chloro-3-carboxy-4-oxo-3,4-dihydro-1,10-phenanthroline;
3-acetyl-18-carboxy-7-hydroxy-4-oxo-3,4-dihydro-1,10-phenanthroline;
3,8-diacety-17-hydroxy-4-oxo-3,4-dihydro-1,10-phenanthroline;
3-carboxy-8-(N-benzyl-N-methylcarbamoyl)-4-oxo-3,4-dihydro-1,10-phenanthroline;
3-carboxy-8-(4-methylpiperidinocarbonyl)-4-oxo-3,4-dihydro-1,10-phenanthroline;
3-carboxy-8-(N-benzyl-N-methylcarbamoyl)-5-fluoro-4-oxo-3,4-dihydro-1,10-phenanthroline;
8-acetyl-3-carboxy-4-oxo-3,4-dihydro-1,10-phenanthroline;
3-carboxy-8-(N-methyl-N-{2-phenylethyl}carbamoyl)-4-oxo-3,4-dihydro-1,10-phenanthroline;
3-carboxy-8-(N-benzyl-N-isopropylcarbamoyl)-4-oxo-3,4-dihydro-1,10-phenanthroline;
3-carboxy-8-(N-benzyl-N-methylcarbamoyl)-7-hydroxy-4-oxo-3,4-dihydro-1,10-phenanthroline;
3-carboxy-8-(N-methyl-N-(4-fluorobenzyl}carbamoyl)-4-oxo-3,4-dihydro-1,10-phenanthroline;
3-carboxy-8-(N-methyl-N-{2,4-difluorobenzyl}carbamoyl)-4-oxo-3,4-dihydro-1,10-phenanthroline;
3-cyano-8-(N-benzyl-N-methylcarbamoyl)-4-oxo-3,4-dihydro-1,10-phenanthroline;
3-carboxy-8-(N,N-diethylcarbamoyl)-4-oxo-3,4-dihydro-1,10-phenanthroline;
3-carboxy-8-(N-benzyl-N-methylcarbamoyl)-5-methyl-4-oxo-3,4-dihydro-1,10-phenanthroline;
8-(N-benzyl-N-methylcarbamoyl)-5-fluoro-3-nitro-4-oxo-3,4-dihydro-1,10-phenanthroline;
8-(N-benzyl-N-methylcarbamoyl)-3,6-dinitro-5-methyl-4-oxo-3,4-dihydro-1,10-phenanthroline;
8-ethoxycarbonyl-3-nitro-4-oxo-3,4-dihydro-1,10-phenanthroline;
8-(N-butyl-N-ethylcarbamoyl)-3-nitro-4-oxo-3,4-dihydro-1,10-phenanthroline;
3-carboxy-6-fluoro-4-oxo-3,4-dihydro-1,10-phenanthroline;
8-(N, N-di-sec-butylcarbamoyl)-3-nitro-4-oxo-3,4-dihydro-1,10-phenanthroline;
8-(N-butyl-N-ethylcarbamoyl)-3-cyano-4-oxo-3,4-dihydro-1,10-phenanthroline;
3-carboxy-8-methoxy-4-oxo-3,4-dihydro-1,10-phenanthroline;
8-(N-cyclohexyl-N-ethylcarbamoyl)-3-nitro-4-oxo-3,4-dihydro-1,10-phenanthroline;
3-carboxy-8-(N-hexyl-N-methylcarbamoyl)-4-oxo-3,4-dihydro-1,10-phenanthroline;
8-(N-hexyl-N-methylcarbamoyl)-3-nitro-4-oxo-3,4-dihydro-1,10-phenanthroline;
6-fluoro-3-nitro-4-oxo-3,4-dihydro-1,10-phenanthroline;

3-carboxy-8-(N-butyl-N-methylcarbamoyl)-4-oxo-3,4-dihydro-1,10-phenanthroline;
3-carboxy-8-(N-ethyl-N-isopropylcarbamoyl)-4-oxo-3,4-dihydro-1,10-phenanthroline;
3-carboxy-8-(N-ethyl-N-propylcarbamoyl)-4-oxo-3,4-dihydro-1,10-phenanthroline;
8-(N-acetylamino)-3-carboxy-4-oxo-3,4-dihydro-1,10-phenanthroline;
3-carboxy-8-(N-{4,4,5,5,5-pentafluoropentyl}-N-methylcarbamoyl)-4-oxo-3,4-dihydro-1,10-phenanthroline;
3-carboxy-8-(N-methyl-N-ethylcarbamoyl)-7-dimethylamino-4-oxo-3,4-dihydro-1,10-phenanthroline;
3-carboxy-8-(N-tert-butoxycarbonylamino)-4-oxo-3,4-dihydro-1,10-phenanthroline;
3-carboxy-6-chloro-8-(N-butyl-N-ethylcarbamoyl)-4-oxo-3,4-dihydro-1,10-phenathroline;
8-amino-7-bromo-3-carboxy-4-oxo-3,4-dihydro-1,10-phenanthroline;
3-carboxy-8-cyano-4-oxo-3,4-dihydro-1,10-phenanthroline;
3-carboxy-8-hydroxy-4-oxo-3,4-dihydro-1,10-phenanthroline;
3-carboxy-8-carboxymethoxy-4-oxo-3,4-dihydro-1,10-phenanthroline;
8-(4-benzylpiperazin-1-ylcarbonyl)-3-nitro-4-oxo-3,4-dihydro-1,10-phenanthroline; or a pharmaceutically-acceptable salt thereof, or a metabolically labile ester derivative of those compounds bearing a carboxy group or groups.

Particularly preferred compounds of the invention include, for example, the following phenanthroline derivatives of the formula (I):
3-[2-(2-methoxyethoxy)ethoxycarbonyl]-4-oxo-3,4-dihydro-1,10-phenanthroline;
8-N-butyl-N-ethylcarbamoyl)-3-carboxy-4-oxo-3,4-dihydro-1,10-phenanthroline;
3,6-dinitro-4-oxo-3,4-dihydro-1,10-phenanthroline;
8-carboxy-3-nitro-4-oxo-3,4-dihydro-1,10-phenanthroline;
8-(4-benzylpiperazin-1-ylcarbonyl)-3-nitro-4-oxo-3,4-dihydro-1,10-phenanthroline;
3-(2,2,2-trifluoroethylsulphonyl)-4-oxo-3,4-dihydro-1,10-phenanthroline;
8-[N-(4-fluorobenzyl)-N-methylcarbamoyl]-3-nitro-4-oxo-3,4-dihydro-1,10-phenantroline;
3-carboxy-8-N,N-diethylthiocarbamoyl-4-oxo-3,4-dihydro-1,10-phenanthroline;
8-(N-benzyl-N-methylcarbamoyl)-3-cyano-5-fluoro-4-oxo-3,4-dihydro-1,10-phenanthroline;
3-acetyl-7-chloro-8-ethoxycarbonyl-4-oxo-3,4-dihydro-1,10-phenanthroline;
3-carboxy-5-fluoro-8-(N-2,2,3,3,4,4,4-heptafluorobutylcarbamoyl)-4-oxo-3,4-dihyro-1,10-phenantroline;
3-carboxy-8-(N-4-ethoxyphenylcarbamoyl)-4-oxo-3,4-dihydro-1,10-phenanthroline;
3-carboxy-8-carbamoyl-4-oxo-3,4-dihydro-1,10-phenanthroline;
3-carboxy-4-oxo-8-(1,2,3,4-tetrahydroisoquinolin-2-ylcarbonyl)-3,4-dihydro-1,10-phenanthroline; or
8-(N-benzyl-N-methylcarbamoyl)-7-dimethylamino-3-ethoxycarbonyl-4-oxo-3,4-dihydro-1,10-phenanthroline; or a pharmaceutically-acceptable salt thereof, or a metabolically labile ester derivative of those compounds bearing a carboxy group.

DETAILED DESCRIPTION OF THE INVENTION

A compound of the invention comprising a phenanthroline derivative of the formula (I) as defined hereinbefore, or a pharmaceutically-acceptable salt thereof, or a metabolically labile ester derivative of substituents $R^1$ and $R^2$ when either, or both, is a carboxy group, may be prepared by any process known to be applicable to the preparation of structurally-related compounds. Such procedures are provided as a further feature of the invention and are illustrated by the examples presented herein in which, unless otherwise stated, $R^1$, $R^2$, $R^3$, $R^4$ and $R^5$ have any of the meanings defined hereinbefore, provided that, when there is an amino, hydroxy or carboxy group in $R^1$, $R^2$, $R^3$, $R^4$ and $R^5$, any such group may optionally be protected by a conventional protecting group which may be removed when so desired by conventional means. A nitrogen heteroatom may also be optionally protected by a conventional protecting group which may be removed when so desired by conventional means.

A suitable protecting group for an amino group is, for example, an acyl group, for example, an alkanoyl group such as acetyl, an alkoxycarbonyl group, for example, a methoxycarbonyl, ethoxycarbonyl or tert-butoxycarbonyl group, an arylmethoxycarbonyl group, for example, benzyloxycarbonyl, or an aroyl group, for example, benzoyl. The deprotection conditions for the above protecting groups necessarily vary with the choice of protecting group. Thus, for example, an acyl group such as an alkanoyl or alkoxycarbonyl group or an aroyl group may be removed, for example, by hydrolysis with a suitable base such as an alkali metal hydroxide, for example, lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris (trifluoroacetate).

A suitable alternative protecting group for a primary amino group is, for example, a phthaloyl group which may be removed by treatment with an alkylamine, for example, dimethylaminopropylamine, or with hydrazine.

A suitable protecting group for a nitrogen heteroatom is, for example, a pivaloyloxymethyl group which may be removed by hydrolysis with a base, for example, sodium hydroxide or ammonia, in a suitable inert solvent or diluent, for example, methanol or ethanol.

A suitable protecting group for a hydroxy group is, for example, an acyl group, for example, an alkanoyl group such as acetyl, an aroyl group, for example, benzoyl, or an arylmethyl group, for example, benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example, lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example, a methyl or an ethyl group which may be removed, for example, by hydrolysis with a base such as sodium hydroxide, or, for example, a tert-butyl group which may be removed, for example, by treatment with an acid, for example, an organic acid such as trifluoroacetic acid, or, for example a benzyl group which may be removed, for example, by hydrogenation over a catalyst such as palladium-on-carbon.

Methods for reactions (a)–(f) are described below:

(a) The reaction of an 8-aminoquinoline derivative with a (1–4C)alkoxymethylene compound of the formula (II)

$$R^1\text{—CO—C}(R^2)\text{=CH—(1–4C)alkoxy} \quad \text{(II)}$$

followed by cyclization of the reaction product; wherein $R^1$ is a (1–4C)alkoxy or a (1–4C)alkyl group; and $R^2$ is a (1–4C)alkoxycarbonyl, (1–4C)alkylsulfonyl, fluoro-(1–4C)alkylsulfonyl or a sulfonylphenyl group; or $R^1$ and $R^2$ are linked, and together with the carbonyl carbon atom to which $R^1$ is attached, and the carbon atom to which $R^2$ is attached, define a 1,3-dioxan-4,6-dione ring (with the carbonyl carbon to which $R^1$ is attached in the 4-position), and which ring is disubstituted in the 2-position by two (1–4C) alkyl groups:

The reaction is preferably carried out in the presence of a suitable solvent such as ethanol. The reaction may also be carried out using neat reagents. The reaction is preferably carried out a temperature in the range 10° C. to 100° C., conveniently in the range 75° C. to 80° C. The cyclization is preferably carried out in the presence of an ether solvent such as, for example, diphenyl ether. The cyclization is preferably carried out at a temperature in the range 180° C. to 270° C., conveniently at, or near, the reflux temperature of the solvent.

The preparation of starting 8-aminoquinoline derivatives is described within the accompanying non-limiting Examples which are provided for the purpose of illustration only. Other necessary 8-aminoquinoline derivatives are obtainable by analogous procedures to those described or by modifications thereto which are within the ordinary skill of an organic chemist. Suitable 8-aminoquinoline derivatives are substituted at the 3-position by any of the $R^2$ substituents defined hereinbefore, at the 4-position by any of the $R^5$ substituents defined hereinbefore, at the 5-position by any of the $R^4$ substituents defined hereinbefore and at the 6-position by any of the $R^3$ substituents defined hereinbefore.

The preparation of certain starting materials of the formula (II) is described within the accompanying Examples. Other necessary starting materials of the formula (II) are obtainable by analogous procedures to those described or by modifications thereto which are within the ordinary skill of an organic chemist. Other necessary starting materials of the formula (II) are obtainable by standard reactions of organic chemistry which are within the ordinary skill of an organic chemist.

(b) For the production of those compounds oftheformula (I) in which each, or both of, the substituents $R^1$ and $R^2$ are carboxy groups, the hydrolysis of a compound of the formula (I) in which each, or both of, the substituents $R^1$ and $R^2$ are (1–6C)alkoxycarbonyl groups:

The hydrolysis is preferably carried out in the presence of a suitable acid or base. The reaction is also preferably carried out in aqueous solution, and at a temperature in the range 10° C. to 110° C., conveniently in the range 80° C. to 100° C. A suitable acid is, for example, a mineral acid such as, for example, hydrochloric acid. A suitable base is, for example, an alkali or alkaline earth metal carbonate or hydroxide, for example, sodium carbonate, potassium carbonate, sodium hydroxide or potassium hydroxide.

The preparation of starting materials of formula (I) in which each, or both of, the substituents $R^1$ and $R^2$ are (1–4C)alkoxycarbonyl groups is described within the accompanying non-limiting Examples which are provided for the purpose of illustration only. Other necessary starting materials are obtainable by analogous procedures to those described or by modifications thereto which are within the ordinary skill of an organic chemist.

(c) For the production of those compounds of the formula (I) which bear a nitro substituent, the nitration of a compound of the formula (I) using a suitable nitrating agent:

A suitable nitrating agent is, for example, concentrated nitric acid in acetic anhydride, concentrated nitric acid in glacial acetic acid or a nitrate salt such as, for example, ammonium nitrate in trifluoroacetic acid.

The reaction is preferably carried out at a temperature in the range 10° C. to 100° C.

(d) The reaction ofa compound of the formula (I) which bears a carboxy substituent, or a reactive derivative thereof, with ammonia, a primary amine or a secondary amine:

The reaction is preferably carried out in an inert solvent or diluent such as, for example, dichloromethane, acetonitrile or dimethylsulfoxide, and at a temperature in the range 0° C. to 100° C. The reaction is also preferably carried out in the presence of a suitable organic amine base such as, for example, triethylamine.

A suitable reactive derivative of a carboxy substituent borne by a compound of the formula (I) is, for example, an acyl halide, for example, an acyl chloride formed by the reaction of the carboxy substituent and an acid chloride, for example, thionyl chloride or oxalyl chloride; a mixed anhydride, for example, an anhydride formed by the reaction of the carboxy substituent and a chloroformate such as isobutyl chloroformate; an active ester, for example, an ester formed by the reaction of the carboxy substituent and a phenol such as pentafluorophenol, an ester such as pentafluorophenyl trifluoroacetate or an alcohol such as $\underline{N}$-hydroxybenzotriazole; an acyl azide, for example, an azide formed by the reaction of the carboxy substituent and an azide such as diphenylphosphoryl azide; an acyl cyanide, for example, a cyanide formed by the reaction of the carboxy substituent and a cyanide such as diethylphosphoryl cyanide; or the product of the reaction of the carboxy substituent and a carbodiimide such as dicyclohexylcarbodiimide.

(e) For the production of those compounds of the formula (I) in which $R^1$ is a (1–4C)alkoxy-(2–4C)alkoxycarbonyl or a (1–4C)alkoxy-(2–4C)alkoxy-(2–4C)alkoxycarbonyl group, the reaction of a compound of the formula (I) bearing an imidazol-1-ylcarbonyl group in the 3-position with a (1–4C)alkoxy-(2–4C)alkanol or a (1–4C)alkoxy-(2–4C) alkoxy-(2–4C)alkanol:

The reaction is preferably carried out in an inert solvent or diluent such as, for example, $\underline{N},\underline{N}$-dimethylformamide, $\underline{N},\underline{N}$-dimethylacetamide, $\underline{N}$-methylpyrrolidin-2-one or dimethylsulfoxide, and at a temperature in the range 0° C. to 150° C., conveniently at or near ambient temperature. The reaction is also preferably carried out in the presence of a suitable base such as, for example, an alkali or alkaline earth metal carbonate, alkoxide, hydroxide or hydride, for example, sodium carbonate, potassium carbonate, sodium ethoxide, potassium butoxide, sodium hydroxide, potassium hydroxide, sodium hydride or potassium hydride, or an organometallic base such as an alkyl-lithium, for example, n-butyl-lithium, or a dialkylamino-lithium, for example, lithium di-isopropylamide, or, for example, an organic amine base such as, for example, pyridine, 2,6-lutidine, collidine, 4-dimethylaminopyridine, triethylamine, morpholine or diazabicyclo-[5.4.0]undec-7-ene.

The preparation of starting materials of the formula (I) bearing an imidazol-1-ylcarbonyl group in the 3-position is described within the accompanying Examples. Other necessary starting materials of the formula (I) bearing an imidazol-1-ylcarbonyl group in the 3-position are obtainable by analogous procedures to those described or by modifications thereto which are within the ordinary skill of an organic chemist.

A suitable value for a (1–4C)alkoxy-(2–4C)alkanol is, for example, 2-methoxyethanol, 2-ethoxyethanol and 3-methoxypropanol. A suitable value for a (1–4C)alkoxy-(2–4C)alkoxy-(2–4C)alkanol is, for example, 2-(2-methoxyethoxy)ethanol, 2-(2-ethoxyethoxy)ethanol and 3-(2-methoxyethoxy)propanol.

(f) For the production of those compounds of the formula (I) in which each, or both of, the substituents $R^1$ and $R^2$ are cyano groups, the dehydration of a compound of the formula (I) in which each, or both of, the substituents $R^1$ and $R^2$ are carbamoyl groups using a suitable dehydrating agent:

The dehydration is preferably carried out at a temperature in the range 0 C. to 100° C., conveniently at or near ambient temperature.

A suitable dehydrating agent is, for example, a mixture of trifluoroacetic anhydride and pyridine, phosphorous pentachloride or phosphorous oxychloride.

The preparation of a compound of the formula (I) in which each, or both of, the substituents $R^1$ and $R^2$ are carbamoyl groups is described, for example, in the section (d) hereinbefore and in the accompanying Examples. Other necessary starting materials of the formula (I) in which each, or both of, the substituents $R^1$ and $R^2$ are carbamoyl groups are obtainable by analogous procedures to those described or by modification thereto which are within the ordinary skill of an organic chemist.

It will be observed that certain phenanthrolinone derivatives of the present invention possess at least one asymmetric carbon atom (for example, when the substituent $R^1$ is, for example, a 1-hydroxyethyl group) and can therefore exist in racemic and optically active forms. It is to be understood that the present invention encompasses a racemic form of any such phenanthroline derivative of the invention, any optically-active form thereof or a mixture thereof which possesses prolyl 4-hydroxylase inhibitory activity. It is a matter of common general knowledge how such optically-active forms may be obtained by stereospecific synthesis or by the separation of mixtures of isomeric compounds.

It is also to be understood that a phenanthroline derivative of the formula (I) may exhibit the phenomenon of tautomerism. In particular, it will be appreciated that the 4-oxo-3,4-dihydro-1,10-phenanthroline group may be in the form, for example, of a 4-hydroxy-1,10-phenanthroline group, or in the form, for example, of a 4-oxo-1,4-dihydro-1,10-phenantroline group.

It is to be understood that the invention encompasses any tautomeric form which possesses prolyl 4-hydroxylase inhibitory activity and is not to be limited merely to any one tautomeric form.

It is also to be understood that certain phenanthroline derivatives of the formula (I) can exist in solvated as well as unsolvated forms such as, for example, hydrated forms. It is to be understood that the invention encompasses all such solvated forms which possess prolyl 4-hydroxylase inhibitory activity.

A suitable pharmaceutically-acceptable salt of a phenanthroline derivative of the invention which is sufficiently basic is an acid-addition salt with, for example, an inorganic or organic acid, for example, hydrochloric, hydrobromic, sulphuric, phosphoric, trifluoroacetic, citric or maleic acid. In addition a suitable pharmaceutically-acceptable salt of a phenanthroline derivative of the invention which is sufficiently acidic is an alkali metal salt, for example, a calcium or magnesium salt, an ammonium or tetra-(2-hydroxyethyl) ammonium salt or a salt with organic amines and quaternary bases which afford a physiologically-acceptable cation, for example, a salt with methylamine, dimethylamine, trimethylamine, ethylenediamine, piperidine, morpholine, pyrrolidine, piperazine, lysine, arginine, guanidine, ethanolamine, triethanolamine, N-methylglucamine, tetramethylammonium, hydroxide or benzyltrimethylammonium hydroxide.

A suitable metabolically labile ester derivative of substituents $R^1$ and $R^2$ when either, or both, is a carboxy group are esters formed with alcohols such as indanol; adamantol; (1–6C)alkanoyloxy-(1–4C)alkanols such as, for example, pivaloyloxymethyl; glycolamides; (5-methyl-2-oxo-1,3-dioxo-4-yl)methyl alcohol, (1–4C)alkoxycarbonyl-(1–4C) alkanols such as, for example, 2-(methoxycarbonyl)ethyl alcohol and oxa-(1–8C)alkandiols such as, for example, 3-oxapentan-1,5-diol and 3,6-dioxaoctan-1,8-diol.

When a pharmaceutically-acceptable salt of a compound of the formula (I) is required, it may be obtained, for example, by reaction of said compound with a suitable acid or base using a conventional procedure. When an optically active form of a compound of the formula (I) is required, it may be obtained by carrying out one of the aforesaid processes using an optically active starting material, or by resolution of a racemic form of said compound using a conventional procedure.

When a metabolically labile ester derivative of substituents $R^1$ and $R^2$ when either, or both, is a carboxy group is required, it may be obtained, for example, by esterifying said carboxy group or groups using a conventional technique.

As stated above, the compounds of the present invention are of potential use in treating fibroproliferative disease, and accordingly the present invention also concerns the use of a compound of the formula (I), including those derivatives hereinbefore excluded from the scope of formula (I), or a pharmaceutically-acceptable salt thereof, or a metabolically labile ester derivative of substituents $R^1$ and $R^2$ when either, or both, is a carboxy group, in the manufacture of a medicament for use in ameliorating fibroproliferative disease. The pharmacological activity may be demonstrated using one or more standard test procedures known in the art or as described in the examples.

A phenanthroline derivative of the present invention may itself be active or it maybe a pro-drug which is converted in vivo to an active compound.

The present invention further provides a pharmaceutical composition comprising one or more phenanthroline derivatives of the formula (I) defined hereinbefore, and in addition those compounds named as excluded hereinbefore, which possess useful pharmacological activity; or a pharmaceutically-acceptable salt or metabolically labile ester thereof. The pharmaceutical composition which may be administered to a warm-blooded animal, including a human, comprises one or more phenanthroline derivatives in association with a pharmaceutically-acceptable diluent or carrier.

A preferred pharmaceutical composition comprises the phenanthroline derivative selected from
3-carboxy-4-oxo-3,4-dihydro-1,10-phenanthroline;
3-carboxy-5-methyl-4-oxo-3,4-dihydro-1,10-phenanthroline;
3-ethoxycarbonyl-4-oxo-3,4-dihydro-1,10-phenanthroline; and
3-ethoxycarbonyl-6-fluoro-4-oxo-3,4-dihydro-1,10-phenanthroline, or a pharmaceutically-acceptable salt thereof, or a metabolically labile ester derivative of the 3-carboxy substituent when present, in association with a pharmaceutically-acceptable diluent or carrier.

A further preferred pharmaceutical composition comprises the phenanthroline derivative, 3-carboxy-4-oxo-3,4-dihydro-1,10-phenanthroline, or a pharmaceutically-acceptable salt thereof or a metabolically labile ester derivative of the 3-carboxy substituent, in association with a pharmaceutically-acceptable diluent or carrier.

The pharmaceutical composition may also comprise a phenanthroline derivative of the formula (I) as defined hereinbefore in the section relating to pharmaceutical compositions, or a pharmaceutically-acceptable salt thereof, or a metabolically labile ester derivative of substituents $R^1$ and $R^2$ when either, or both, is a carboxy group, a pharmaceutically-accepted diluent or carrier.

A suitable cyclodextrin is, for example, α-cyclodextrin, β-cyclodextrin or α-cyclodextrin. An alternative suitable cyclodextrin is, for example, a cyclodextrin derivative such as 2-hydroxypropyl-β-cyclodextrin, an alkylated cyclodextrin or a branched cyclodextrin. Preferably, the cyclodextrin is 62-cyclodextrin.

The composition may be in a form suitable for oral use, for example, a tablet, capsule, aqueous or oily solution, suspension or emulsion; for topical use, for example, a cream, ointnent, gel or aqueous or oily solution or suspension; for nasal use, for example, a snuff, nasal spray or nasal drops; for vaginal or rectal use, for example, a suppository; for administration by inhalation, for example, as a finely divided powder such as a dry powder, a microcrystalline form or a liquid aerosol; for sub-lingual or buccal use, for example, a tablet or capsule; or for parenteral use (including intravenous, subcutaneous, intramuscular, intravascular or infuision), for example, a sterile aqueous or oily solution, emulsion or suspension.

Alternatively, the composition may be a continuous release composition as either a solid or liquid depot formulation, as microparticles or as microparticulate suspensions. In general the above compositions may be prepared in a conventional manner using conventional excipients. It is to be understood that the pharmaceutical composition may comprise a prodrug of a phenanthroline derivative of the formula (I) as defined hereinbefore in the section relating to pharmaceutical compositions. Such prodrugs include, but are not limited to, metabolically labile ester derivatives of $R^1$ and $R^2$ when either, or both, is a carboxy group; other substituents, for example, hydroxy groups, may provide suitable positions for the formation of prodrugs. The preparation of suitable prodrugs is within the ordinary skill of a worker in the pharmaceutical sciences.

As stated above, the present invention concerns the use of a compound of the present invention, or a pharmaceutically-acceptable salt thereof, or a metabolically labile ester derivative of substituents $R^1$ and $R^2$ when either, or both, is a carboxy group, in combatting fibroproliferative disease. Other agents are currently known to possess activity against one or more fibroproliferative diseases. Thus, for example, cyclooxygenase inhibitory non-steroidal anti-inflammatory agents (NSAIA), such as indomethacin, acetylsalicyclic acid, ibuprofen, sulindac, tolmetin and piroxicam, are used in the treatment of rheumatoid arthritis. Also certain anti-inflammatory steroidal agents such as corticosteroidal agents, for example, beclomethasone dipropionate, betamethasone valerate, prednisolone or triamcinolone are used in the treatment of rheumatoid arthritis. Co-administration of a prolyl 4-hydroxylase inhibitor of the present invention with a NSAIA or a steroid derivative as defined hereinbefore can result in a reduction of the dose of the latter agents which is needed to produce a therapeutic effect. According to a further feature of the present invention there is provided a pharmaceutical composition which comprises a phenanthroline derivative of the formula (I) as defined hereinbefore in the section relating to pharmaceutical compositions, or a pharmaceutically-acceptable salt thereof, or a metabolically labile ester derivative of substituents $R^1$ and $R^2$ when either, or both, is a carboxy group, as defined hereinbefore, in conjunction or admixture with a cyclooxygenase inhibitory non-steroidal anti-inflammatory agent or an anti-inflammatory steroidal agent, and a pharmaceutically-acceptable diluent or carrier.

In addition certain agents are beneficial in the treatment of liver fibrosis, for example, certain alkaloids such as colchicine and β-adrenergic receptor blocking agents such as propranolol, atenolol, labetolol and metoprolol may be beneficial. Co-administration of a 4-prolyl hydroxylase inhibitor of the present invention with colchicine or a β-adrenergic receptor blocking agent can result in an improved therapeutic effect. According to a further feature of the present invention there is provided a pharmaceutical composition which comprises a phenanthroline derivative of the formula (I) as defined hereinbefore in the section relating to pharmaceutical compositions, or a pharmaceutically-acceptable salt thereof, or a metabolically labile ester derivative of substituents $R^1$ and $R^2$ when either, or both, is a carboxy group, as defined hereinbefore, in conjunction or admixture with colchicine or a β-adrenergic receptor blocking agent, and a pharmaceutically-acceptable diluent or carrier.

The phenanthroline derivative will normally be administered to a warm-blooded animal at a unit dose within the range 5–5000 mg per square meter body area of the animal, i.e. approximately 1–100 mg/kg, and this normally provides a therapeutically-effective dose. A unit dose form such as a tablet or capsule will usually contain, for example, 1–250 mg of active ingredient. Preferably a daily dose in the range of 0.1–5 mg/kg is employed. However, the daily dose will necessarily be varied depending upon the host treated, the particular route of administration, and the severity of the illness being treated. Accordingly the optimum dosage may be determined by the practitioner who is treating any particular patient.

According to a further feature of the invention there is provided a phenanthroline derivative of the formula (I) as defined hereinbefore in the section relating to pharmaceutical compositions, or a pharmaceutically-acceptable salt thereof, or a metabolically labile ester derivative of substituents $R^1$ and $R^2$ when either, or both, is a carboxy group, for use in a method of therapeutic treatment of the human or animal body.

According to a further preferred feature of the invention there is provided the phenanthroline derivative selected from 3-carboxy-4-oxo-3,4-dihydro-1,10-phenanthroline;
3-carboxy-5-methyl-4-oxo-3,4-dihydro-1,10-phenanthroline;
3-ethoxycarbonyl-4-oxo-3,4-dihydro-1,10-phenanthrolline; and
3-ethoxycarbonyl-6-fluoro-4-oxo-3,4-dihydro-1,10-phenanthroline, or a pharmaceutically-acceptable salt thereof, or a metabolically labile ester derivative of the 3-carboxy substituent when present, for use in a method of therapeutic treatment of the human or animal body.

According to a further preferred feature of the invention there is provided the phenanthroline derivative 3-carboxy-4-oxo-3,4-dihydro-1,10-phenanthroline, or a pharmaceutically-acceptable salt thereof, or a metabolically labile ester derivative of the 3-carboxy substituent, for use in a method of therapeutic treatment of the human or animal body.

According to a further feature of the present invention there is provided a method for producing an anti-fibroproliferative effect in a warm-blooded animal, such as man, in need of such treatment which comprises administering to said animal an effective amount of a phenanthroline derivative of the formula (I) as defined hereinbefore in the section relating to pharmaceutical compositions, or a pharmaceutically-acceptable salt thereof, or a metabolically labile ester derivative of substituents $R^1$ and $R^2$ when either, or both, is a carboxy group.

According to a further preferred feature of the invention there is provided a method for producing an anti-fibroproliferative effect in a warm-blooded animal, such as man, in need of such treatment which comprises administering to said animal an effective amount of the phenanthroline derivative selected from 3-carboxy-4-oxo-3,4-dihydro-1,10-phenanthroline,
 3-carboxy-5-methyl-4-oxo-3,4-dihydro-1,10-phenanthroline;
3-ethoxycarbonyl-4-oxo-3,4-dihydro-1,10-phenanthroline; and
 3-ethoxycarbonyl-6-fluoro-4-oxo-3,4-dihydro-1,10-phenanthroline , or a pharmaceutically-acceptable salt thereof, or a metabolically labile ester derivative of the 3-carboxy substituent when present.

According to a further preferred feature of the invention there is provided a method for producing an anti-fibroproliferative effect in a warm-blooded animal, such as man, in need of such treatment which comprises administering to said animal an effective amount of the phenanthroline derivative 3-carboxy-4-oxo-3,4-dihydro-1,10-phenanthroline or a pharmaceutically-acceptable salt thereof, or metabolically labile ester derivative of the 3-carboxy substituent.

The invention also provides the use of a phenanthroline derivative of the formula (I) as defined hereinbefore in the section relating to pharmaceutical compositions, or a pharmaceutically-acceptable salt thereof, or a metabolically labile ester derivative of substituents $R^1$ and $R^2$ when either, or both, is a carboxy group, in the manufacture of a novel medicament for use in the production of an anti-fibroproliferative effect in a warm blooded animal, such as man.

According to a further preferred feature of the invention there is provided the use of the phenanthroline derivative selected from
3-carboxy-4-oxo-3,4-dihydro-1,10-phenanthroline;
3-carboxy-5-methyl-4-oxo-3,4-dihydro-1,10-phenanthroline;
3-ethoxycarbonyl-4-oxo-3,4-dihydro-1,10-phenanthroline; and
3-eth6xycarbonyl-6-fluoro-4-oxo-3,4-dihydro-1,10-phenanthroline, or a pharmaceutically-acceptable salt thereof, or a metabolically labile ester derivative of the 3-carboxy substituent when present, in the manufacture of a novel medicament for use in the production of an anti-fibroproliferative effect (for example for treating the formation of scar tissue following injury or surgery) in a warm blooded animal, such as man.

According to a further preferred feature of the invention there is provided the use of the phenanthroline derivative 3-carboxy-4-oxo-3,4-dihydro-1,10-phenanthroline, or a pharmaceutically-acceptable salt thereof, or a metabolically labile ester derivative of the 3-carboxy substituent, in the manufacture of a novel medicament for use in the production of an anti-fibroproliferative (for example for treating the formation of scar tissue following injury or surgery) effect in a warm blooded animal, such as man.

The invention is illustrated but not limited by the following Examples in which unless otherwise stated.

EXAMPLES (i) evaporations were carried out by rotary evaporation in vacuo and work-up procedures were carried out after removal of residual solids by filtration;

(ii) operations were carried out at ambient temperature, that is in the range 18–20° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 reversed-phase silica (Art. 9303) obtained from E. Merck, Darmstadt, Germany;

(iv) yields are given for illustration only and are not necessarily the maximum attainable;

(v) the end-products of the formula (I) generally have satisfactory microanalysis and their structures were confirmed by NMR and mass spectral techniques [proton magnetic resonance spectra were determined using a Jeol FX 90Q or a Bruker AM200 spectrometer operating at a field strength of 200 MHz; chemical shifts are reported in parts per million downfield from tetramethysilane as an internal standard (δ scale) and peak multiplicities are shown thus: s, singlet, d, doublet; dd, doublet of doublets; t, triplet, m, multiplet; fast-atom bombardment (FAB) mass spectral data were obtained using a VG Analytical MS9 spectrometer and xenon gas and, where appropriate, either positive ion data or negative ion data were collected];

(vi) intermediates were not generally fully characterised and purity was assessed by thin layer chromatographic, infra-red (IR) or NMR analysis;

(vii) melting points were determined using a Mettler SP62 automatic melting point apparatus, a Koffler hot plate apparatus or an oil-bath apparatus; and (viii) the following abbreviations have been used:

| | |
|---|---|
| THF | tetrahydrofuran; |
| DMF | N,N-dimethylformamide; |
| DMSO | dimethylsulfoxide; and |
| TFA | trifluoroacetic acid. |

Example 1

1,1'-Carbonyldiimidazole (30.4 g) was added to a stirred mixture of 3-carboxy-4-oxo-3,4-dihydro-1,10-phenanthroline (18 g) and DMF (400 ml). The mixture was stirred at 100° C. for 2.5 hours, and then cooled to ambient temperature. The resulting solid was filtered to give 3-(imidazol-1-ylcarbonyl)-4-oxo-3,4-dihydro-1,10-phenanthroline in 92% yield.

Sodium hydride (3.15 g, 60%) was added in portions to a mixture of 2-(2-methoxyethoxy)ethanol (15 ml) and DMF (200 ml). The mixture was stirred for approximately 30 minutes until effervescence ceased. 3-(Imidazol-1-ylcarbonyl)-4-oxo-3,4-dihydro-1,10-phenanthroline (21.05 g) was added and the mixture stirred for 18 hours. The mixture was acidified to pH 5–6 with acetic acid, and evaporated to dryness under reduced pressure. Water (50 ml) was added and the mixture extracted with dichloromethane. The organic layer was washed with brine, dried ($MgSO_4$) and evaporated to dryness under reduced pressure. The residue was purified by flash chromatography on silica using dichloromethane, followed by a 24:1:0.1 mixture of dichloromethane methanol : triethylamine as eluant. The product so obtained was triturated with ethyl acetate to give 3-[2-(2-methoxyethoxy)ethoxycarbonyl]-4-oxo-3,4-dihydro-1,10-phenanthroline in 68% overall yield, mp 164–165° C.

NMR Spectrum (D6-DMSO+D4-HOAc): 3.22(s,3H); 3.45(m,2H); 3.58(m,2H); 3.7(t,3H); 4.3 (t,2H); 7.75(dd,2H); 7.8(d,2H); 8.2(d,2H); 8.48(dd,2 8.55(s,1H); 9.05(dd,1H).

The 3-carboxy-4-oxo-3,4-dihydro-1,10-phenanthroline used as starting material was obtained as follows:

A mixture of 8-aminoquinoline (14.4 g) and diethyl ethoxymethylenemalonate (26 g) in ethanol (100 ml) was heated at reflux for 18 hours. The mixture was cooled, filtered and the solid washed with ethanol. The solid so obtained was added to refluxing diphenyl ether (1000 ml), and the resulting mixture stirred at reflux for 45 minutes. The mixture was cooled to approximately 60° C. and diluted with hexane (500 ml). The mixture was cooled to ambient temperature, filtered and the solid washed with hexane to give 3-ethoxycarbonyl-4-oxo-3,4-dihydro-1,10-phenanthroline in 84% yield, mp 242–244° C.

A mixture of 3-ethoxycarbonyl-4-oxo-3,4-dihydro-1,10-phenanthroline (20 g) and 5M hydrochloric acid (100 ml) was stirred at reflux for 2 hours. The mixture was cooled and filtered. The solid so obtained was recrystallised from DMF to give the required starting material in 95% yield.

NMR Spectrum (D6-DMSO): 7.88(m,1H); 8.0(d,1H); 8.25(d,1H); 8.6(m,1H); 8.72(m,1H); 9.12 (m, 1H).

Example 2

A mixture of 8-N-butyl-N-ethylcarbamoyl)-3-ethoxycarbonyl-4-oxo-3,4-dihydro-1,10-phenanthroline (12 g) and 2M hydrochloric acid (300 ml) was stirred at reflux for 2 hours. The mixture was cooled to ambient temperature, filtered and the solid washed with water. The solid so obtained was recrystallised from acetonitrile to give 8-(N-butyl-N-ethylcarbamoyl)-3-carboxy-4-oxo-3,4-dihydro-1,10-phenanthroline in 76% yield, mp 236–237° C.

NMR Spectrum (D6-DMSO-at 100° C.): 0.86(t,3H); 1.18 (t,3H); 1.30(q,2H) 1.63(m,2H); 8.08(d,1H); 8.35(d,1H); 8.60(d,1H); 8.82(s,1H); 9.08 (d, 1H).

The 8-(N-butyl-N-ethylcarbamoyl)-3-ethoxycarbonyl-4-oxo-3,4-dihydro-1,10-phenanthroline used as starting material was obtained as follows:

A mixture of 2-nitroaniline (41.4 g) and diethyl ethoxymethylenemalonate (66 ml) was heated on a steam bath for 24 hours. The hot reaction mixture was treated with ethanol (300 ml), cooled and filtered to give diethyl (2-nitroanilino) methylenemalonate in 88% yield, mp 104–105° C.

Diethyl (2-nitroanilino)methylenemalonate (43 g) was added to refluxing diphenyl ether (600 ml). The mixture was stirred at reflux for 1.5 hours, then cooled to ambient temperature. Diethyl ether (600 ml) was added and the mixture filtered. The solid so obtained was washed with diethyl ether to give 3-ethoxycarbonyl-8-nitro-4-oxo-3,4-dihydroquinoline in 85% yield, mp 241–243° C.

A mixture of 3-ethoxycarbonyl-8-nitro-4-oxo-3,4-dihydro-quinoline (12 g) and 2M sodium hydroxide solution (100 ml) was stirred at reflux for 1 hour. The mixture was cooled to ambient temperature and acidified to pH 5 with glacial acetic acid. The mixture was filtered and the solid so obtained washed with water to give 3-carboxy-8-nitro-4-oxo-3,4-dihydroquinoline in 93% yield, mp 263–265° C.

DMF (0.2 ml) was added to a mixture of 3-carboxy-8-nitro-4-oxo-3,4-dihydroquinoline (30 g) and thionyl chloride (150 ml) and the mixture stirred at reflux for approximately 2 hours until a clear solution was obtained. The solution was evaporated to dryness under reduced pressure, the residue dissolved in toluene and the solution again evaporated to dryness under reduced pressure. N-ethylbutylamine (19.1 ml, 14.14 g) followed by triethylamine (30 ml) were added dropwise to a stirred, ice-cold solution of the residue so obtained in acetonitrile. The mixture was stirred at ambient temperature for 1 hour and then evaporated to dryness under reduced pressure. The residue was partitioned between water and ethyl acetate. The orgainc layer was dried (MgSO$_4$) and evaporated to dryness under reduced pressure. The residue was purified by flash chromatography on silica using a 1:19 mixture of ethyl acetate:chloroform as eluant. There was thus obtained 3-N-butyl-N-butyl-ethylcarbamoyl)-4-chloro-8-nitro-quinoline in 93% yield.

Ammonium formate (26.5 g) was added in portions to a stirred mixture of 3-(N-butyl-N-ethylcarbamoyl)-4-chloro-8-nitro-quinoline (40 g), 10% palladium on carbon (20 g) and ethanol (500 ml) at reflux. The mixture was stirred at relux for 1 hour, the hot mixture was filtered through a pad of celite and the filtrates evaporated to dryness. The residue was partitioned between water and chloroform and the organic layer dried, and evaporated to dryness under reduced pressure. There was thus obtained 3-(N-butyl-N-ethylcarbamoyl)-8-amino-quinoline in 99% yield.

A mixture of 3(N-butyl-N-ethylcarbamoyl)-8-amino-quinoline (25 g) and diethyl ethoxymethylenemalonate (23.8 g) in ethanol was heated at reflux for 18 hours. The mixture was evaporated to dryness under reduced pressure and the residue purified by flash chromatography on silica using chloroform, followed by 1:19 mixture of methanol:chloroforn as eluant. The solvent was evaporated and the residue obtained on standing was added to refluxing diphenyl ether (500 ml). The mixture was stirred at reflux for 1.5 hours, then cooled to ambient temperature and added to a stirred 1:1 mixture of hexane:ether (500 ml). The mixture was stirred for 18 hours, filtered and the solid so obtained washed with diethyl ether to give the required starting material in 55% yield, mp 128–129° C.

Example 3

A solution of concentrated nitric acid (1 ml) in acetic anhydride (10 ml) was added dropwise to a stirred mixture of 4-oxo-3,4-dihydro-1,10-phenanthroline (0.98 g) in acetic anhydride (10 ml) The mixture was stirred at ambient temperature for 3 hours, diluted with ethyl acetate (50ml) and filtered. The solid so obtained was recrystallised from a mixture of DMF and ethyl acetate to give 3,6-dinitro-4-oxo-3,4-dihydro-1,10-phenanthroline in 50% yield.

NMR Spectrum (D6-DMSO): 8.08(dd,1H); 8.92(s,1H); 8.95(s,1H); 9.06(dd, 1H); 9.23 (dd, 1H).

Example 4

A mixture of 8-ethoxycarbonyl-3-nitro-4-oxo-3,4-dihydro-1,10-phenanthroline (0.55 g) and 2M sodium hydroxide solution (5 ml) was stirred at reflux for 2 hours. The hot suspension was neutralised with glacial acetic acid, cooled and diluted with water. The mixture was filtered and washed with water to give 8-carboxy-3-nitro-4-oxo-3,4-dihydro-1,10-phenanthroline in 98% yield.

NMR Spectrum (D6-DMSO):.8.1(d,1H); 8.35(d,1H); 8.98(s,1H); 9.06(d,1H); 9.5(d,1H).

The 8-ethoxycarbonyl-3-nitro-4-oxo-3,4-dihydro-1,10-phenanthroline used as starting material was obtained as follows:

A mixture of 3-ethoxycarbonyl-8-nitro-4-oxo-3,4-dihydro-quinoline (10.2 g) and phosphorous oxychloride (10 ml) was stirred at reflux for 2 hours. The warm reaction mixture was added cautiously to a vigorously stirred mixture of ice, concentrated aqueous ammonia and chloroform. The organic layer was separated, washed with water, dried and evaporated to dryness. The residue was purified by flash chromatography on silica using chloroform as eluant to give 4-chloro-3-ethoxycarbonyl-8-nitro-quinoline in 75% yield, mp 253–254° C.

Ammonium formate was added to a vigorously stirred mixture of 4-chloro-3-ethoxycarbonyl-8-nitro-quinoline (5.6 g), ethanol (1000 ml) and 10% palladium on carbon catalyst (2 g). The mixture was stirred at ambient temperature for 1 hour, filtered through a pad of celite and the pad washed with dichloromethane. The combined filtrate and washings were evaporated to dryness. The residue so obtained was purified by flash chromatography on silica using chloroform as eluant to give 3-ethoxycarbonyl-8-amino-quinoline in 58% yield, mp 94–96° C.

A mixture of 3-ethoxycarbonyl-8-amino-quinoline (9. 9 g), 2, 2-dimethyl-5-methoxymethylene-1,3-dioxan-4,6-dione (*Monatsh. Chem.*, 98:564–78 (1967))(10.3 g) and ethanol (80 ml) was stirred at reflux for 2 hours. The mixture was cooled and filtered. The solid so obtained was washed with ethanol to give 8-(2,2-dimethyl-4,6-dioxo-1,3-dioxan-5-ylideneamino)-3-ethoxycarbonylquinoline in 80% yield, mp 228–231° C.

The solid was added in portions over 5 minutes to stirred diphenyl ether at 260° C. and stirring was continued for 30 minutes. The mixture was cooled to ambient temperature and diluted with hexane (200 ml). The mixture was filtered to give 8-ethoxycarbonyl-4-oxo-3,4-dihydro-1,10-phenanthroline as a solid in 73% yield, mp 250–252° C.

A mixture of 8-ethoxycarbonyl-4-oxo-3,4-dihydro-1,10-phenanthroline (0.8 g), ammonium nitrate (0.26 g) and trifluoroacetic acid (10 ml) was stirred at reflux for 6 hours. Further portions (0.26 g) of ammonium nitrate were added after 2 hours and 4 hours at reflux. The mixture was cooled to ambient temperature and stirred whilst water (50 ml) was added. The mixture was filtered and the solid so obtained was stirred with a 1:1 mixture of ethanol:chloroform. The mixture was filtered to give the required starting material as a solid in 60% yield.

Example 5

A mixture of 8-carboxy-3-nitro-4-oxo-3,4-dihydro-1,10-phenanthroline (228 mg), thionyl chloride (5 ml) and DMF (0.1 ml) was stirred at reflux for 3 hours. The mixture was cooled to ambient temperature and evaporated to dryness. The residue was dissolved in dichloromethane (10 ml) and the solution stirred whilst a solution of N-benzylpiperazine (158 mg) and triethylamine (1 ml) in dichloromethane was added over 5 minutes. The mixture was stirred for 1 hour, washed with water, dried and evaporated to dryness. A solution of the residue in DMSO (3 ml) and water (0.5 ml) was heated at 90° C. for 18 hours. After cooling to ambient temperature, the solution was treated with water (20 ml) and ethyl acetate (5 ml) and the mixture filtered. The residue was recrystallised from a mixture of methanol and chloroform to give 8-(4-benzylpiperazin-1-ylcarbonyl)-3-nitro-4-oxo-3,4-dihydro-1,10-phenanthroline as a solid in 42% yield, mp 213–216° C.

NMR Spectrum (D6-DMSO): 2.54(m,4H); 3.55–3.7(m, 6H); 7.2–7.4(m,5H) 8.0(d,1H); 8.35(d,1H); 8.58(d,1H); 8.97 (s,1H); 9.08(d,1H).

Example 6

8-[2-Methoxycarbonyl-2-(2,2,2-trifluoroethylsulfonyl)-ethenylaino]quinoline (4 g) was added to diphenyl ether (100 ml) with stirring at 260° C., and stirring was continued for 2 hours. The mixture was allowed to cool to ambient temperature and hexane (100 ml) was added. The mixture was filtered, and the residue purified by flash chromatography on silica using increasingly polar mixtures of methanol and chloroform as eluant. The product so obtained was recrystallised from acetic acid to give 3-(2,2,2-trifluoroethyl-sulphonyl)-4-oxo-3,4-dihydro-1,10-phenanthroline, mp 272–274° C.

NMR Spectrum (D6-DMSO): 4.87(q,2H); 8.0(dd,1H); 8.03(d,1H); 8.25(d, 1H); 8.52(d, 1H); 8.64(m, 1H) ; 9.15(dd, 1H).

The 8-[2-methoxycarbonyl-2-(2,2,2-trifluoroethylsulphonyl)-ethenylamino]quinoline used as starting material was obtained as follows:

3-Chloroperbenzoic acid (22.2 g, 60%) was added in portions to a stirred solution of methy-2-(2,2,2-trifluoroethylthio)acetate (*J Med. Pharm. Chem.*, 5:491 (1962))(6 g) in dichloromethane (120 ml). The mixture was stirred at ambient temperature for 24 hours and then filtered. The filtrate was washed successively with aqueous sodium hydrogen sulphite, aqueous sodium carbonate and brine, dried and evaporated to dryness. There was thus obtained methyl 2-(2,2,2-trifluoroethylsulfonyl)acetate in 84% yield as a solid, mp 59–60° C.

A mixture of 8-aminoquinoline (1.87 g), triethyl orthoformate (2.4 ml) and methyl 2-(2,2,2-trifluoroethylsulfonyl) acetate (2.86 g) was stirred at reflux for 30 minutes. The mixture was cooled to ambient temperature and diethyl ether (20 ml) added. The mixture was filtered to give the required starting material in 86% yield, mp 221–223° C.

Example 7

A mixture of 8-[N-(4-fluorobenzyl)-N-methylcarbamoyl]-4-oxo-3,4-dihydro-1,10-phenanthroline (0.3 g), glacial acetic acid (5 ml) and concentrated nitric acid (0.15 ml) was heated at 90° C. for 18 hours. The mixture was cooled to ambient temperature and water (20 ml) and ethyl acetate (10 ml) were added. The mixture was filtered, and the solid so obtained recrystallised from a mixture of DMF and ethyl acetate. There was thus obtained 8-[N-(4-fluorobenzyl)-N-methylcarbamoyl]-3-nitro-4-oxo-3,4-dihydro-1,10-phenanthroline in 27% yield, mp 294–296° C.

NMR Spectrum (D6-DMSO): 3.12(s,3H); 4.7(s,2H); 7.15 (m,2H); 7.4(m,2H) 7.98 (d,1H); 8.36 (d, 1H); 8.62 (d, 1H); 8.98 (s, 1H); 9.12 (d, 1H).

The 8-[N-(4-fluorobenzyl)-N-methylcarbamoyl]-4-oxo-3,4-dihydro-1,10- phenanthroline used as starting material was obtained as follows:

Using a procedure analogous to that described in Example 2 in the section relating to the prepartion of starting materials 3-carboxy-8-nitro-4-oxo-3,4-dihydroquinoline was reacted with N-(4-fluorobenzyl)-N-methylamine to give 3-[N-(4-fluorobenzyl)-N-methylcarbamoyl]-4-chloro-8-nitroquinoline in 89% yield, mp 135–137° C.

Using a procedure analogous to that described in Example 2 in the section relating to the prepartion of starting materials 3-[N-(4-fluorobenzyl)-N-methylcarbamoyl]-4-chloro-8-nitroquinoline was hydrogenated to give 3-[N-(4-fluorobenzyl)-N-methylcarbamoyl]-8-aminoquinoline in 99% yield.

Using a procedure analogous to that described in Example 2 in the section relating to the preparation of starting materials 3-[N-(4-fluorobenzyl)-N-methylcarbamoyl]-8-aminoquinoline was reacted with diethyl ethoxymethylenemalonate to give 3-ethoxycarbonyl-8-[N-(4-fluorobenzyl)-N-methylcarbamoyl]-4-oxo-3,4-dihydro-1,10-phenanthroline in 64% yield, mp 206–207° C.

Using a procedure analogous to that described in Example 2 in the section relating to the prepartion of starting materials 3-ethoxycarbonyl-8-[N-(4-fluorobenzyl)-N--methylcarbamoyl]-4-oxo-3,4-dihydro-1,10-phenanthroline was hydrolysed. The product so obtained was recrystallised from acetic acid to give 3-carboxy-8-[N-(4-fluoro-benzyl)-N-methylcarbamoyl]-4-oxo-3,4-dihydro-1,10-phenanthroline, mp 245–246° C.

A solution of 3-carboxy-8-[N-(4-fluorobenzyl)-N-methylcarbamoyl]-4-oxo-3,4-dihydro-1,10-phenanthroline (0.5 g) in diphenyl ether (3 ml) was stirred at reflux for 6 hours. The mixture was cooled and filtered. The solid so obtained was washed with hexane and purified by flash chromatography on silica using increasingly polar mixtures of methanol and ethyl acetate as eluant. There was thus obtained the required starting material.

Example 8

Using a procedure analogous to that described in Example 2,3-ethoxycarbonyl-8-N,N-diethylthiocarbamoyl-4-oxo-3,4-dihydro-1,10-phenanthroline was hydrolysed. The product so obtained was recrystallised from a mixture of methanol and chloroform to give 3-carboxy-8-N,N-diethylthiocarbamoyl-4-oxo-3,4-dihydro-1,10-phenanthroline.

NMR Spectrum (D6-DMSO at 100° C.): [mixture of rotamers] 1.1–1.5(m,6H); 3.4–4.3(m,4H); 8.04(d,1H); 8.35 (d,1H); 8.42(d,1H); 8.82(s,1H); 9.0(d,1H).

The 3-ethoxycarbonyl-8-N,N-diethylthiocarbamoy-4-oxo-3,4-dihydro-1,10-phenanthroline used as starting material was obtained as follows:

Using a procedure analogous to that described in Example 2 in the section relating to the preparation of starting materials 3-carboxy-8-nitro-4-oxo-3,4-dihydroquinoline was reacted in turn with thionyl chloride and diethylamine, and was hydrogenated to give 8-amino-3-N,N-diethylcarbamoylquinoline in 71% yield.

A mixture of 8-amino-3-N,N-diethylcarbamoylquinoline (1.22 g), toluene (10 ml) and Lawesson's Reagent (1.22 g) was stirred at reflux for 2 hours. The mixture was evaporated to dryness and the residue purified by flash chromatography on silica using increasingly polar mixtures of methanol and chloroform. There was thus obtained 8-amino-3-N,N-diethylthiocarbamoylquinoline in 100% yield.

Using a procedure analogous to that described in Example 2 in the section relating to the preparation of starting materials 8-amino-3-N,N-diethylthiocarbamoylquinoline was reacted with diethyl ethoxymethylenemalonate, and then refluxed with diphenyl ether to give the required starting material in 47% yield.

Example 9

Trifluoroacetic anhydride (0.5 ml) was added dropwise to a stirred, ice-cooled mixture of 8-(N-benzyl-N-methylcarbamoyl)-3-carbamoyl-4-chloro-5-fluoro-1,10-phenanthroline (0.3 g) in pyridine (3 ml). The mixture was stirred at ambient temperature for 1 hour. The mixture was acidified with 3M hydrochloric acid and stirred at ambient temperature for 18 hours. The mixture was filtered and the solid so obtained recrystallised from a mixture of methanol and ethyl acetate to give 8-(N-benzyl-N-methylcarbamoyl)-3-cyano-5-fluoro-4-oxo-3,4-dihydro-1,10-phenanthroline in 24% yield, mp 267–269° C.

NMR Spectrum (D6-DMSO at 100° C.): 3.05(s,3H); 4.7(s,2H); 7.3–7.5(m,5H) 7.65(d,1H); 8.5(s,1H); 8.55(d, 1H); 9.05(d,1H).

The 8-(N-benzyl-N-methylcarbamoyl)-3-carbamoyl-4-chloro-5-fluoro-1,10-phenanthroline used as starting material was obtained as follows:

Using an analogous procedure to that described in Example 2 in the section relating to the preparation of starting materials 4-fluoro-2-nitroaniline and diethyl ethoxymethylenemalonate were reacted, and then refluxed in diphenyl ether to give 3-ethoxycarbonyl-6-fluoro-8-nitro-4-oxo-3,4-dihydroquinoline in 45% yield, mp 278–280° C.

Using an analogous procedure to that described in Example 2 in the section relating to the preparation of starting materials 3-ethoxycarbonyl-6-fluoro-8-nitro-4-oxo-3,4-dihydroquinoline was hydrolysed to give 3-carboxy-6-fluoro-8-nitro-4-oxo-3,4-dihydroquinoline in 84% yield, mp 254–256° C.

Using an analogous procedure to that described in Example 2 in the section relating to the preparation of starting materials 3-carboxy-6-fluoro-8-nitro-4-oxo-3,4-dihydroquinoline was reacted with thionyl chloride and then N-benzylmethylamine to give 3-[N-benzyl-N-methylcarbamoyl]-4-chloro-6-fluoro-8-nitroquinoline in 63% yield.

Using an analogous procedure to that described in Example 2 in the section relating to the preparation of starting materials 3-[N-benzyl-N-methylcarbamoyl]-4-chloro-6-fluoro-8-nitroquinoline was hydrogenated to give 8-amino-3 [N-benzyl-N-methylcarbamoyl]-6-fluoroquinoline 63% yield.

Using an analogous procedure to that described in Example 2 in the section relating to the preparation of starting materials 8-amino-3 -N-benzyl-N-methylcarbamoyl]-6-fluoroquinoline was reacted with diethyl ethoxymethylenemalonate, and then refluxed in diphenyl ether. The product so obtained was recrystallised from a mixture of ethyl acetate and hexane to give 3-ethoxycarbonyl-8-(N-benzyl-N-methylcarbamoyl)-5-fluoro-4-oxo-3,4-dihydro-1,10-phenanthroline in 70% yield, mp 201–203° C.

Using an analogous procedure to that described in Example 2,3-ethoxycarbonyl-8-(N-benzyl-N-methylcarbamoyl)-5-fluoro-4-oxo-3,4-dihydro-1,10-phenanthroline was hydrolysed. The product so obtained was recrystallised from acetic acid to give 3-carboxy-8-(N-benzyl-N-methylcarbamoyl)-5-fluoro-4-oxo-3,4-dihydro-1, 10-phenanthroline in 81 % yield, mp 168–171° C.

A mixture of 3-carboxy-8-(N-benzyl-N-methylcarbamoyl)-5-fluoro-4-oxo-3,4-dihydro-1,10-phenanthroline (0.7 g) and thionyl chloride was stirred at reflux for 30 minutes, and then evaporated to dryness. A solution of concentrated ammonia (2 ml) and triethylamine (5 ml ) in acetonitrile (25 ml) were added to the residue, and the mixture stirred at ambient temperature for one hour. The mixture was evaporated to dryness, and the residue stirred with water (10 ml) and ethyl acetate (10 ml). The mixture was filtered and the product so obtained recrystallised from a mixture of methanol and ethyl acetate. There was thus obtained the required starting material in 69% yield, mp 180–183° C.

Example 10

A mixture of 8-amino-4-chloro-3-ethoxycarbonylquinoline (0.3 g) and ethyl 2-ethoxymethyleneacetoacetate (Annalen, 1897, 297, 16, 0.25 g) was heated at 90° C. for 2.5 hours. The mixture was cooled to ambient temperature and the resulting solid added to diphenyl ether at reflux. The mixture was refluxed for 45 minutes, and cooled to 60° C. The mixture was diluted with carbon tetrachloride (50 ml) and cooled to ambient temperature with stirring. The mixture was filtered and the solid so obtained purified by flash chromatography on silica using increasingly polar mixtures of methanol and chloroform. The product so obtained was recrystallised from methanol to give 3-acetyl-7-chloro-8-ethoxycarbonyl-4-oxo-5 3,4-dihydro-1,10-phenanthroline in 29% yield, mp 288–290° C.

NMR Spectrum (D6-DMSO): 1.4(t,3H); 2.66(s,3H); 4.5 (q,2H); 8.2(d,1H); 8.45(d,1H); 8.5(d,1H ; 9.27(s,1H).

The 8-amino-4-chloro-3-ethoxycarbonylquinoline used as starting material was obtained as follows:

A mixture of 4-chloro-3-ethoxycarbonyl-8-nitroquinoline (1.4 g), ethanol (10 ml), triethylamine (0.7 ml) and 10% palladium on carbon catalyst (0.2 g) was stirred under an atmosphere of hydrogen for 2.5 hours. The mixture was filtered and the filtrate was evaporated to dryness. The residue was purified by MPLC on silica using chloroform as eluant to give the required starting material in 24% yield, mp 110–112° C.

Example 11

Using an analogous procedure to that described in Example 2,3-ethoxycarbonyl-5-fluoro-8-(N-2,2,3,3,4,4,4-heptafluorobutylcarbamoyl)-4-oxo-3,4-dihydro-1,10-phenanthroline was hydrolysed to give 3-carboxy-5-fluoro-8-(N-2,2,3,3,4,4,4-heptafluorobutylcarbamoyl)-4-oxo-3,4-dihydro-1,10-phenanthroline in 46% yield.

NMR Spectrum (D6-DMSO): 4.2–4.45(2H,m); 7.9(1H, d); 8.76(1H,s) 9.0(1H,d); 9.42(1H,d) 9.65(1H,t).

The 3-ethoxycarbonyl-5-fluoro-8(N-2,2,3,3,4,4,4-heptafluorobutylcarbamoyl)-4-oxo-3,4-dihydro-1,10-phenanthroline used as starting material was obtained as follows:

Using an analogous procedure to that described in Example 2 in the section relating to the preparation of starting materials 3-carboxy-6-fluoro-8-nitro-4-oxo-3,4-dihydroquinoline was reacted with thionyl chloride and then 2,2,3,3,4,4,4-heptafluorobutylamine to give 3-[N-2,2,3,3,4,4,4-heptafluorobutylcarbamoyl]-4-chloro-6-fluoro-8-nitroquinoline in 33% yield, mp 159–160° C.

Using an analogous procedure to that described in Example 2 in the section relating to the preparation of starting materials 3-[N-2,2,3,3,4,4,4-heptafluorobutylcarbamoyl]-4-chloro-6-fluoro-8-nitroquinoline was hydrogenated to give 8-amino-6-fluoro-3-[N-2,2,3,3,4,4,4-heptafluorobutylcarbamoyl]quinoline in 73% yield, mp 202–204° C.

Using an analogous procedure to that described in Example 2 in the section relating to the preparation of starting materials 8-amino-6-fluoro-3-[N-2,2,3,3,4,4,4-heptafluorobutylcarbamoyl]quinoline was reacted with diethyl ethoxymethylenemalonate, and then refluxed in diphenyl ether. There was thus obtained the required starting material in 87% yield, mp 288–290 C.

Example 12

Using an analogous procedure to that described in Example 2 3-ethoxycarbonyl-8-(N-4-ethoxyphenylcarbamoyl)-4-oxo-3,4-dihydro-1,10-phenanthroline was hydrolysed. The product so obtained was recrystallised from DMF to give 3-carboxy-8-(N-4-ethoxyphenyl-carbamoyl)-4-oxo-3,4-dihydro-1,10-phenanthroline in 41% yield.

NMR Spectrum (D6-DMSO+TFA): 1.27(3H,t); 4.0(2H, m); 6.85(2H,m); 7.65(2H,m); 7.98(1H,d ); 8.28(1H,d); 8.75 (1H,s) ; 9.0(1H,d), 9.45(1H,d).

The 3-ethoxycarbonyl-8-(N-4-ethoxyphenylcarbamoyl)-4-oxo-3,4-dihydro-1,10-phenanthroline used as starting material was obtained as follows:

Using an analogous procedure to that described in Example 2 in the section relating to the preparation of starting materials 3-carboxy-8-nitro-4-oxo-3,4-dihydroquinoline was reacted with thionyl chloride and then 4-ethoxyaniline to give 3-[N-4-ethoxyphenylcarbamoyl]-4-chloro-8-nitroquinoline in 43% yield, mp 232–233° C.

Using an analogous procedure to that described in Example 2 in the section relating to the preparation of starting materials 3-[N-4-ethoxyphenylcarbamoyl]-4-chloro-8-nitroquinoline was hydrogenated to give 8-amino-3-[N-4-ethoxyphenylcarbamoyl]quinoline in 74% yield, mp 187–189° C.

Using an analogous procedure to that described in Example 2 in the section relating to the preparation of starting materials 8-amino-3-[N-4-ethoxyphenylcarbamoyl] quinoline was reacted with diethyl ethoxymethylenemalonate, and then refluxed in diphenyl ether. There was thus obtained the required starting material in 70% yield.

Example 13

Using an analogous procedure to that described in Example 2,3-ethoxycarbonyl-8-carbamoyl-1-oxo-3,4-dihydro-1,10-phenanthroline was hydrolysed. The product so obtained was recrystallised from DMF to give 3-carboxy-8-carbamoyl-4-oxo-3,4-dihydro-1,10-phenanthroline in 96% yield.

NMR Spectrum (D6-DMSO): 7.9(broad s,1H); 8.1(d,1H); 8.22(d,1H); 8.5(broad s,1H); 8.75(S, 1H); 9.05(d,1H); 9.5 (d,1H).

The 3-ethoxycarbonyl-8-carbamoyl-4-oxo-3,4-dihydro-1, 10-phenanthroline used as starting material was obtained as follows:

Using an analogous procedure to that described in Example 2 in the section relating to the preparation of starting materials 3-carboxy-8-nitro-4-oxo-3,4-dihydroquinoline was reacted with thionyl chloride and then concentrated aqueous ammonia. The product so obtained was recrystallised from ethanol to give 3-carbamoyl-4-chloro-8-nitroquinoline in 79% yield, mp 277–279° C.

Using an analogous procedure to that described in Example 2 in the section relating to the preparation of starting materials 3-carbamoyl-4-chloro-8-nitroquinoline was hydrogenated to give 8-amino-3-carbamoylquinoline in 54% yield, mp 164–165° C.

Using an analogous procedure to that described in Example 2 in the section relating to the preparation of starting materials 8-amino-3-carbamoylquinoline was reacted with diethyl ethoxymethylenemalonate, and then refluxed in diphenyl ether. There was thus obtained the required starting material in 64% yield.

Example 14

Using an analogous procedure to that described in Example 2,3-ethoxycarbonyl-4-oxo-8-(1,2,3,4- tetrahydroisoquinolin-2-ylcarbonyl)-3,4-dihydro-1,10-phenanthroline was hydrolysed. The product so obtained was recrystallised from a mixture of methanol and chloroform to give 3-carboxy-4-oxo-8-(1,2,3,4-tetrahydroisoquinolin-2-ylcarbonyl)-3,4-dihydro-1,10-phenanthroline in 72% yield, mp 171–182° C.

NMR Spectrum (D6-DMSO at 100° C. IC) 2.96(t,2H); 3.82(t,2H); 4.8(s,2H) 7.7(m,4H);

8.1(d,1H); 8.4(d,1H): 8.72(d,1H); 8.85(s,1H); 9.18(d,1H).

The 3-ethoxycarbonyl-4-oxo-8-(1,2,3,4-tetrahydroisoquinolin-2-ylcarbonyl)-3,4-dihydro-1,10-phenanthroline used as starting material was obtained as follows:

Using an analogous procedure to that described in Example 2 in the section relating to the preparation of starting materials 3-carboxy-8-nitro-4-oxo-3,4-dihydroquinoline was reacted with thionyl chloride and then 1,2,3,4-tetrahydroisoquinoline to give 3-(1,2,3,4-tetrahydroisoquinolin-2-ylcarbonyl)-4-chloro-8-nitro-quinoline in 71% yield.

Using an analogous procedure to that described in Example 2 in the section relating to the preparation of starting materials 3-(1,2,3,4-tetrahydroisoquinolin-2-ylcarbonyl)-4-chloro-8-nitro-quinoline was hydrogenated to give 8-amino-3-(1,2,3,4-tetrahydroisoquinolin-2-ylcarbonyl)quinoline in 100% yield.

Using an analogous procedure to that described in Example 2 in the section relating to the preparation of starting materials 8-amino-3-(1,2,3,4-tetrahydroisoquinolin-2-ylcarbonyl)quinoline was reacted with diethyl ethoxymethylenemalonate, and then refluxed in diphenyl ether. There was thus obtained the required starting material in 50% yield, mp 238–240° C.

Example 15

A mixture of 8-amino-3-(N-benzyl-N-methylcarbamoyl)-4-dimethylaminoquinoline (1.28 g), diethyl ethoxymethyl-enemalonate (1 g) and ethanol (5 ml) was heated at reflux for 2 hours. The mixture was evaporated to dryness and a solution of the residue in diphenyl ether (70 ml) was stirred at ref lux for 1 hour. The mixture was cooled to ambient temperature and stirred whilst a 1:2 mixture (200 ml) of diethyl ether:hexane was added. The mixture was filtered and the solid so obtained recrystallised from ethyl acetate. There was thus obtained 8 -(N-benzyl-N-methylcarbainoyl)-7-dimethylamino-3-ethoxy-carbonyl-4-oxo-3,4-dihydro-1, 10-phenanthroline in 80% yield, mp 169–170° C.

NMR Spectrum (D6-DMSO): 1.3(m,3H); 2.85–3.35(m, 9H); 4.25(m,2H); 4.35–5.3(m,2H); 7.2–7.5(m,5H); 8.0(d, 1H); 8.15(m,1H); 8.5(m,1H); 8.62(s,1H).

The 8-amino-3-(N-benzyl-N-methylcarbamoyl)-4-dimethylamino-quinoline used as starting material was obtained as follows:

Using an analogous procedure to that described in Example 2 in the section relating to the preparation of starting materials 3-carboxy-8-nitro-4-oxo-3,4-dihydroquinoline was reacted with thionyl chloride and then N-benzylmethylamine. The product so obtained was recrystallised from ethanol to give 3-(N-benzyl-N-methylcarbamoyl)-4-chloro-8-nitroquinoline in 82% yield, mp 120–121° C.

A mixture of 3-N-benzyl-N-methylcarbamoyl)-4-chloro-8-nitroquinoline (1.42 g), ethanol (20 ml) and a 33% solution of dimethylamine in ethanol (5 ml) was heated at 90° C. for 6 minutes. The mixture was evaporated to dryness and the residue was partitioned between water and ethyl acetate. The organic layer was dried and evaporated to dryness. The residue was dissolved in ethanol and 10% palladium on carbon catalyst (0.3 g) and ammonium formate (1 g) were added to the solution. The mixture was stirred at reflux for 2 hours, and the mixture filtered. The filtrate was evaporated to dryness and the residue was partitioned between water and ethyl acetate. The organic layer was dried and evaporated to dryness to give the required starting material in 96% yield, which was used without further purification.

Example 16

Biological Data

Top assess the enzymatic activity of compounds of the present invention, the following assays ((a)–(d)) were used:

(a) An in vitro enzyme assay system, which assesses the inhibitory properties of a test compound in a cell free system using a highly purified preparation of prolyl 4-hydroxylase. The enzyme preparation was obtained using the method described by N. Kedersha and R. Berg (*Collagen Related Research*, 1:345 (1981)) and the activity of a test compound was measured using the method described by C. J. Cunliffe, T. J. Franklin and R. Gaskell (*Biochem.J.*, 240:617 (1986)).

(b) An in vitro assay system involving incubating embryonic chick tendon cells in the presence of a test compound and measuring the inhibition of hydroxylation at the 4-position of prolyl residues within the available collagen. The embryonic chick tendon cells were prepared from the leg tendons of 17-day chick embryos using the method of P. Dehm and D. Prockop (*Biochem. Biophys Acta*, 240:358 (1971)). The cells were incubated in the presence of [$^{14}$C]- and [$^{3}$H]-labelled L-proline and the extent of hydroxylation at the 4-transposition of the prolyl residues within the collagen was determined using the procedure described by T. J. Franklin and M. Hitchen (Biochem. J., 261:127–130 (1989)). (c) An in vitro assay involving incubating cultures of 3T6 cells with a test compound and [$^{14}$C]- and [$^{3}$H]-labelled L-proline, and measuring the inhibition of hydroxylation at the 4-trans-position of prolyl residues within the available collagen using the procedure described by T. J. Franklin and M. Hitchen (Biochem. J., 261:127–130 (1989)).

(d) An in vivo assay involving the measurement of the inhibition by a test compound of hydroxylation at the 4-trans-position of prolyl residues within collagen within the uteri of immature (20–21 day) female rats. The test compounds were administered either orally or intraperitoneally to the rats in which uterine collagen synthesis had been stimulated by the subcutaneous administration of a solution of oestradiol benzoate (0.5 µg on each of two successive days) in arachis 14 oil. The rats were dosed with 5 µCuries of [$^{14}$C]-L-proline and the uteri were taken 2 hours after the dosing of the radiolabelled proline and sonicated. Collagen was extracted by treatment of the tissue with water at 120° C. for 1 hour in an autoclave and hydrolysed by treatment with 6N hydrochloric acid for 18 hours at reflux temperature. The proline and 4-hydroxyproline residues were separated by column chromatography on a reversed-phase Spherisorb S5ODSI column using as eluent a 89.9:10:0.1 v/v mixture of water: isopropanol: trifluoroacetic acid to which 0.3% w/v of sodium dodecylsulphate had been added. The ratio of radioactivity found in each of the proline and 4-hydroxyproline fractions was determined by liquid scintillation counting to allow the measurement of the inhibition of hydroxylation by a test compound.

The compound described in Example 2 has an IC$_{50}$ of 0.4 μM in test (a), an IC$_{50}$ of 1.2 μM in test (b), an IC$_{50}$ of 5.4 μM in test (c) and an inhibition of 46% at 50 mg/kg orally (compound dosed 2 hours before proline administration) in test (d).

Example 17

The following illustrate representative pharmaceutical dosage forms containing the compound of the formula (I) as defined hereinbefore in the section relating to pharmaceutical composition, or a pharmaceutically-acceptable salt thereof, or a metabolically labile ester derivative of substituents R$^1$ and R$^2$ when either, or both, is a carboxy group (hereafter compound X), for therapeutic or prophylactic use in humans:

| Tablet I | mg/tablet |
|---|---|
| Compound X | 100 |
| Lactose Ph. Eur. | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound X | 50 |
| Lactose Ph. Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound X | 1.0 |
| Lactose Ph. Eur. | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound X | 10 |
| Lactose Ph. Eur. | 488.5 |
| Magnesium stearate | 1.5 |

| Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| Ointment | /ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

The above formulations may be obtained by conventional procedures well known in the pharmaceutical art. The tablets (a)–(c) may be enteric coated by conventional means, for example, to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

We claim:

1. A compound of formula (I):

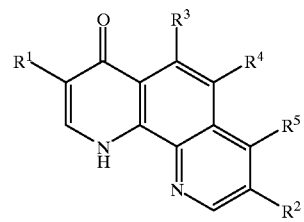

wherein R$^1$ is hydrogen, carboxy or a metabolically labile ester derivative thereof, cyano, halo, nitro, amino, (1–4C)alkyl, (1–4C)alkylamino, di-(1–4C)alkylamino, (1–6C)alkoxycarbonyl, (2–4C)alkanoyl, hydroxy-(1–4C)alkyl, carbamoyl, N-(1–4C)alkylcarbamoyl, (1–4C)alkylthio, (1–4C)alkylsulfinyl, (1–4C)alkylsulfonyl; phenylthio, phenylsulfinyl or phenylsulfonyl said phenyl being optionally substituted with 1 to 4 substituents selected from halo, (1–4C)alkyoxy, (1–4C)alkyl, cyano, hydroxy and trifluoromethyl; fluoro-(1–4C)alkylthio, fluoro-(1–4C)alkylsulfinyl, fluoro-(1–4C)alkylsulfonyl, (1–4C)alkoxy-(2–4C)alkoxycarbonyl, N,N-di-[(1–4C)alkyl]carbamoyl-(1–4C)alkoxycarbonyl, (1–4C)alkylamino-(2–4C)

alkoxycarbonyl, di-(1–4C)alkylamino-(2–4C) alkoxycarbonyl, (1–4C)alkoxy-(2–4C)alkoxy-(2–4C) alkoxycarbonyl, (2–4C)alkanoyloxy-1–4C)alkyl or N-[amino-(2–8C)alkyl]carbamoyl;

$R^2$ is hydrogen, hydroxy, amino, cyano, halo, (1–4C) alkyl, carboxy or a metabolically labile ester derivative thereof, (1–4C)alkylamino, di-(1–4C)alkylamino, (1–6C)alkoxycarbonyl, (2–4C)alkanoyl, (1–4C)alkoxy, carboxy-(1–4C)alkoxy, (1–4C)alkoxycarbonyl-(1–4C) alkoxy, carbamoyl, N-(1–8C)alkylcarbamoyl, N,N-di-(1–8C)alkylcarbamoyl, N-[amino-(2–8C)alkyl] carbamoyl, N-[(1–4C)alkylamino-(1–8C)alkyl] carbamoyl, N-[di-(1–4C)alkylamino-(1–8C)alkyl] carbamoyl, N-cyclohexylcarbamoyl, N-[cyclopentyl] carbamoyl, N-(1–4C)alkylcyclohexylcarbamoyl or N-(1–4C)alkylcyclopentylcarbamoyl; N-phenylcarbamoyl, N-(1–4C)alkyl-N-phenylcarbamoyl, N,N-diphenylcarbamoyl, N-[phenyl-(1–4C)alkyl]carbamoyl, N-(1–4C)alkyl-N-[phenyl-(1–4C)alkyl]carbamoyl, or N, N-di-[phenyl-(1–4C)alkyl]carbamoyl said phenyl or phenyl groups being optionally substituted with 1 to 4 substituents selected from halo, (1–4C)alkyoxy, (1–4C)alkyl, cyano, hydroxy and trifluoromethyl; N-[(2–4C) alkanoyl]carbamoyl, N-[(1–4C)alkoxycarbonyl] carbamoyl, N-[fluoro-(2–6C)alkyl]carbamoyl, N,N-[fluoro-(2–6C)alkyl]-N-(1–4C)alkylcarbamoyl or N, N-[di-fluoro-(2–6C)alkyl]carbamoyl; pyrrolidin-1-ylcarbonyl, piperidinocarbonyl, piperazin-1-ylcarbonyl or morpholinocarbonyl wherein the heterocyclic group is optionally substituted with 1 to 4 substituents selected from (1–4C)alkyl and benzyl; 1,2,3,4-tetrahydro-isoquinolin-2-ylcarbonyl, N,N-[di-(1–4C) alkyl]thiocarbamoyl, N-(2–4C)alkanoylamino or N-[(1–- 4)alkoxycarbonyl]amino;

$R^3$ and $R^4$, which may be the same or different, are hydrogen, (1–4C)alkyl, (2–4C)alkoxy, halo, nitro, hydroxy, fluoro-(1–4C)alkyl or pyridinyl;

or $R^4$ is methoxy; and $R^5$ is hydrogen, hydroxy, amino, (1–4C)alkylamino, di-(1–4C)alkylamino, halo, (1–4C)alkoxy-(2–4C)alkoxy or fluoro-(1–6C)alkoxy; pyrrolidin-1-yl, piperidino, piperazin-1-yl or morpholino wherein the heterocyclic group is optionally substituted with 1 to 4 substituents selected from (1–4C)alkyl and benzyl; or a pharmaceutically-acceptable salt thereof;

provided that:

where $R^1$ is carboxy and $R^3$ and $R^4$ are hydroxy; $R^2$ and $R^5$ are not together H;

where $R^1$ is ethoxycarbonyl; $R^2$, $R^3$, $R^4$ and $R^5$ are not together H;

where $R^1$ is ethoxycarbonyl and $R^4$ is F; $R^2$, $R^3$ and $R^5$ are not together H where $R^1$ is carboxy and $R^3$ is H or alkyl; $R^2$, $R^4$ and $R^5$ are not together H;

where $R^3$ is OH; $R^1$, $R^2$, $R^3$ and $R^5$ are not together H;

where $R^5$ is OH, $R^3$ is H or alkyl, and $R^4$ is H; $R^1$ and $R^2$ are not together ethoxycarbonyl, carboxy, methoxycarbonyl or H; and where $R^5$ is $-N(CH_3)_2$; $R^1$, $R^2$, $R^3$ and $R^4$ are not together H.

2. A compound of claim 1 wherein $R^1$ is hydrogen, carboxy or a metabolically labile ester derivative thereof, cyano, nitro, amino, (1–4C)alkyl, (1–4C)alkylamino, di-(1-4-C)alkylamino, (1–6C)alkoxycarbonyl, (1–4C) alkylthio, (1–4C)alkylsulfinyl or (1–4—C)alkylsulfonyl; phenylthio, phenylsulfinyl or phenylsulfonyl said phenyl being optionally substituted with 1 to 2 substituents selected from (1–4C)alkoxy, halo, hydroxy and trifluoromethyl; fluoro-(1–4C)alkylsulfinyl, fluoro-(1–4C)alkylsulfonyl, (1–4C)alkoxy- -(2–4C)alkoxycarbonyl, N,N-di-[(1–4C) alkyl]carbamoyl-(1-414C)alkoxycarbonyl, (1–4C) alkylamino-(2–4C)alkoxycarbonyl, di-(1–4C)alkylamino-(2–4C)alkoxycarbonyl, (1–4C)alkoxy-(2–4C)alkoxy-(2–4C)alkoxycarbonyl, (2–4C)alkanoyloxy-(1–4C)alkyl or N-[amino-(2–4C)alkyl]carbamoyl.

3. A compound of claim 2 wherein $R^1$ is hydrogen, carboxy or a metabolically labile ester derivative thereof, cyano, halo, nitro, amino, (1–6C)alkoxycarbonyl, (2–4C) alkanoyl, hydroxy-(1–4C)alkyl, (1–4C)alkylsulfonyl, phenylsulfonyl said phenyl being optionally substituted with 1 to 2 substituents selected from (1–4C)alkoxy, halo, hydroxy and trifluoromethyl; N-[amino-(2–4C)alkyl]carbamoyl, fluoro-(1–4C)alkylsulfonyl, (1–4C)alkoxy-(2–4C) alkoxycarbonyl, N,N-di-[(1–4C)alkyl]carbamoyl-(1–4C) alkoxycarbonyl, (1–4C)alkoxy-(2–4C)alkoxy-(2–4C) alkoxycarbonyl or (2–4C)alkanoyloxy-(1–4C)alkyl.

4. A compound of claim 1 wherein $R^1$ is carboxy or a metabolically labile ester derivative thereof, cyano, nitro, (1–6C)alkoxycarbonyl, (2–4C)alkanoyl, fluoro-(1–4C) alkylsulfonyl or (1–4C)alkoxy-(2–4C)alkoxy-(2–4C) alkoxycarbonyl.

5. A compound of claim 1 wherein $R^2$ is hydrogen, hydroxy, amino, cyano, carboxy or a metabolically labile ester derivative thereof, (1–6C)alkoxycarbonyl, (2–4C) alkanoyl, (1–4C)alkoxy, carboxy-(1–4C)alkoxy, carbamoyl, N-[amino-(2–8C)alkyl]carbamoyl, N,N-di-(1–8C) alkylcarbamoyl or N-(1–4C)alkyl-N-cyclohexylcarbamoyl; N-phenylcarbamoyl, N-(1–4C)alkyl-N-phenylcarbamoyl, N-[phenyl-(1–4C)alkyl]carbamoyl, N-(1–4C)alkyl-N-[phenyl-(1–4C)alkyl]carbamoyl or N,N-di-[phenyl-(1–4C) alkyl]carbamoyl said phenyl or phenyl groups being optionally substituted with 1 to 2 substituents selected from (1–4C)alkoxy, halo, hydroxy and trifluoromethyl; N-[(2–4C)alkanoyl]carbamoyl, N-[fluoro-(2–6C)alkyl] carbamoyl or N-[fluoro-(2–6C)alkyl)-N-(1–4C) alkylcarbamoyl; pyrrolidin-1-ylcarbonyl, piperidinocarbonyl or piperazin-1-ylcarbonyl wherein the heterocyclic group is optionally substituted with 1 to 2 substituents selected from (1–4C)alkyl and benzyl; 2,3,4-tetrahydroisoquinolin-2-ylcarbonyl, N-(2–4C) alkanoylamino, N-[di-(1–4C)alkoxycarbonyl]amino or N, N-[di-(1–4C)alkyl]thiocarbamoyl.

6. A compound of claim 1 wherein $R^2$ is hydrogen, carboxy or a metabolically labile ester derivative thereof, (1–6C)alkoxycarbonyl, carbamoyl or N,N-di-(1–8C) alkylcarbamoyl; N-phenylcarbamoyl or N-(1–4C)alkyl-N-[phenyl-(1–4C)alkyl]carbamoyl said phenyl being optionally substituted with 1to 2substituents selected from (1–4C) alkoxy, halo, hydroxy and trifluoromethyl; N-[fluoro-(2–6C) alkyl)carbamoyl, 1,2,3,4; -tetrahydro-isoquinolin-2ylcarbonyl, piperazin-1-ylcarbonyl wherein the heterocyclic group is optionally substituted with 1to 2substituents selected from (1–4C)alkyl and benzyl; or N,N-[di-(1–4C)alkyl]thiocarbamoyl.

7. A compound of claim 1 wherein $R^2$ is hydrogen, hydroxy, carboxy or a metabolically labile ester derivative thereof, carboxy-(1–4C)alkoxy, carbamoyl, N-(1–8C) alkylcarbamoyl, N-di-(1–8C)alkylcarbamoyl, N, N-[amino-(2–8C)alkyl]carbamoyl, N-[(1–4C)alkylamino-(1–8C) alkyl]carbamoyl, N-[di-(1–4C)alkylamino-(1–8C)alkyl] carbamoyl, N-[(2–4C)alkanoyl]carbamoyl, piperazin-1- ylcarbonyl wherein the heterocyclic group is optionally substituted with 1to 2substituents selected from (1–4C)alkyl and benzyl; morpholinocarbonyl, N-(2–4C)alkanoylamino or N-[(1–4C)alkoxycarbonyl]amino.

8. A compound of claim 1 wherein $R^3$ and $R^4$, which may be the same or different, are hydrogen, (1–4C)alkyl, halo, pyridinyl, fluoro-(1–4C)alkyl, nitro or hydroxy.

9. A compound of claim 8 wherein $R^3$ and $R^4$, which may be the same or different, are hydrogen, (1–4C)alkyl, halo or pyridinyl.

10. A compound of claim 1 wherein $R^3$ and $R^4$, which may be the same or different, are hydrogen, halo or nitro.

11. A compound of claim 1 wherein $R^3$ is hydroxy.

12. A compound of claim 1 wherein $R^5$ is hydrogen, hydroxy, pyrrolidin-1-yl wherein the heterocyclic group is optionally substituted with 1 to 2 substituents selected from (1–4C)alkyl and benzyl; di-(1–4C)alkylamino, (1–4C)alkylamino, halo, (1–4C)alkoxy-(2–4C)alkoxy or fluoro-(1–6C)alkoxy.

13. A compound of claim 1 wherein $R^5$ is hydrogen, di-(1–4C)alkylamino or halo.

14. A compound of claim 1 wherein $R^5$ is hydrogen, hydroxy or piperazin-1-yl wherein the heterocyclic group is optionally substituted with 1 to 2 substituents selected from (1–4C)alkyl and benzyl.

15. A compound of claim 1 wherein
$R^1$ is hydrogen, carboxy or a metabolically labile ester derivative thereof, cyano, nitro, amino, bromo, methoxycarbonyl, ethoxycarbonyl, acetyl, 2,2,2-trifluoroethyl sulfonyl, 2-[2-methoxyethoxy]ethoxycarbonyl, 1-hydroxyethyl, carbamoyl, methyl sulfonyl, phenylsulfonyl said phenyl being optionally substituted with 1to 2 substituents selected from ethoxy, fluoro and trifluoromethyl; N-(6-aminohexyl) carbamoyl, 2-methoxyethoxycarbonyl, N,N-diethylcarbamoylmethoxycarbonyl or propionyloxymethyl;

$R^2$ is hydrogen, hydroxy, amino, cyano, carboxy or a metabolically labile ester derivative thereof, methoxycarbonyl, ethoxycarbonyl, acetyl, carbamoyl, methoxy, carboxymethoxy, N-(6-aminohexyl) carbamoyl, N-ethyl-N-butylcarbamoyl, N-diethylcarabamoyl, N,Ndi-sec-butylcarbamoyl, N-methyl-N-butylcarbamoyl, N-methyl-N-hexylcarbamoyl, N-ethyl-N-propylcarbaamoyl, N-ethyl-N-isopropylcarbaamoyl, N-ethyl-N-pentylcarbamoyl or N-ethyl-N-cyclohexylcarbamoyl; N-phenylcarbamoyl, N-methyl-N-phenylcarbamoyl, N-(2-phenylethyl)carbamoyl, N-methyl-N-benzylcarbamoyl, N-methyl-N-(2-phenylethyl)carbamoyl, N-isopropyl-N-benzylcarbamoyl, N-ethyl-Nbenzylcarbamoyl or N,N-dibenzylcarbamoyl said phenyl or phenyl groups being optionally substituted with 1 to 2 substituents selected from ethoxy, fluoro and trifluoromethyl; N-[2,2,3,3,4,4,4-heptafluorobutyl]carbamoyl, N-[2,2,3,3,4,4,4-heptafluorobutyl]-N-methylcarbamoyl, N-[4,4,5,5, 5-pentafluoropentyl]-N-methylcarbamoyl or 1,2,3,4-tetrahydro-isoquinolin-2-ylcarbonyl; pyrrolidin-1-ylcarbonyl, piperidinocarbonyl or piperazin-1-ylcarbonyl wherein the heterocyclic group is optionally substituted with methyl or benzyl; N,N-diethylthiocarbamoyl, N-acetylamino or N-tert-butoxycarbonylamino;

$R^3$ and $R^4$, which may be the same or different, are hydrogen, fluoro, chloro, bromo, nitro, hydroxy, pyridin-4-yl, trifluoromethyl or methyl;

$R^5$ is hydrogen, dimethylamino, diethylamino, chloro, bromo, hydroxy, pyrrolidin-1-yl wherein the heterocyclic group is optionally substituted with methyl or benzyl; methylamino, 2-methoxyethoxy, 2,2,2-trifluoroethoxy or 4,4,5,5,5-pentafluoropentoxy.

16. A compound of claim 1 wherein
$R^1$ is hydrogen, carboxy or a metabolically labile ester derivative thereof, cyano, nitro, methyl, ethyl, methoxycarbonyl, ethoxycarbonyl, methylamino, ethylamino, dimethylamino, 2,2,2-trifluoroethylsulfonyl or 2,2,2-trifluoroethylsulfinyl; phenylsulfinyl, phenylsulfonyl or phenylthio said phenyl being optionally substituted with 1 to 2 substituents selected from ethoxy, fluoro and trifluoromethyl; methylthio, methylsulfinyl, methylsulfonyl, 2-[2-methoxyethoxy]ethoxycarbonyl, N-(6-aminohexyl) carbamoyl, 2-methoxyethoxycarbonyl, 2-(methylamino) ethoxycarbonyl, 2-(dimethylamino) ethoxycarbonyl, N,N-diethylcarbamoylmethoxycarbonyl or propionyloxymethyl;

$R^2$ is hydrogen, hydroxy, carboxy or a metabolically labile ester derivative thereof, carbamoyl, carboxymethoxy, N-(6-aminohexyl)carbamoyl, N-ethylcarbamoyl, N-ethyl-N-butylcarbamoyl, N-butylcarbamoyl, N,N-diethylcarbamoyl, N,N-di-sec-butylcarbamoyl, N-methyl-N-butylcarbamoyl, N-methyl-N-hexylcarbamoyl, N-ethyl-N-propylcarbamoyl, N-ethyl-N-isopropylcarbamoyl, N-ethyl-N-pentylcarbamoyl, piperazin-1-ylcarbonyl wherein the heterocyclic group is optionally substituted with methyl or benzyl; N-[methylaminomethyl] carbamoyl, N-[dimethylaminomethyl]carbamoyl, N-acetylcarbamoyl, morpholinocarbonyl, N-acetylamino or N-tert-butoxycarbonylamino;

$R^3$, and $R^4$, which may be the same or different, are hydrogen, fluoro, chloro, bromo, methyl or pyridin-4-yl; or $R^3$ is hydroxy; and $R^5$ is hydrogen, hydroxy or piperazin-1-yl.

17. A compound of claim 15 wherein $R^1$ is carboxy or a metabolically labile ester derivative thereof, cyano, nitro, ethoxycarbonyl, acetyl, 2,2,2-trifluoroethylsulfonyl or 2-[2-methoxyethoxy]ethoxycarbonyl;

$R^2$ is hydrogen, carboxy, ethoxycarbonyl, carbamoyl, N-ethyl-N-butylcarbamoyl, N-(4-ethoxyphenyl) carbamoyl, N-methyl-N-benzylcarbamoyl, N-methyl-N-4-fluorobenzylcarbamoyl, N-[2,2,3,3,4,4,4-heptafluorobutyl]carbamoyl, 1,2,3,4-tetrahydro-isoquinolin-2-ylcarbonyl, 4-benzylpiperazin-1-ylcarbonyl or N,N-diethylthiocarbamoyl;

$R^3$ and $R^4$, which may be the same or different, are hydrogen, fluoro or nitro; and $R^5$ is hydrogen, dimethylamino or chloro.

18. A compound of claim 1:
3,8-dicarboxy-4- oxo-3,4-dihydro-1,10-phenanthroline;
8-carboxy-4-oxo-3,4-dihydro-1,10-phenanthroline;
3-nitro-4-oxo-3,4-dihydro-1,10-phenanthroline;
3-cyano-4-oxo-3,4-dihydro-1,10-phenanthroline;
3-cyano-5-hydroxy-4-oxo-3,4-dihydro-1,10-phenanthroline;
5-chloro-3-cyano-4-oxo-3,4-dihydro-1,10-phenanthroline;
5-chloro-3-ethoxycarboxyl-4-oxo-3,4-dihydro-1,10-phenanthroline;
5-chloro-3-carboxy-4-oxo-3,4-dihydro-1,10-phenanthroline;
3-acetyl-8-carboxy-7-hydroxy-4-oxo-3,4-dihydro-1,10-phenanthroline;
3-diacetyl-7-hydroxy-4-oxo-3,4-dihydro-1,10-phenanthroline; or 3-carboxy-8-(N-benzyl-N-methylcarbamoyl)-4-oxo-3,4-dihydro-1,10-phenanthroline; or a pharmaceutically-acceptable salt thereof, or a metabolically labile ester derivative of those compounds bearing a carboxy group or groups.

19. A compound of claim 1:
3-carboxy-8-(4-methylpiperidinocarbonyl)-4-oxo-3,4-dihydro-1,10-phenanthroline;
3-carboxy-8-(N-benzyl-N-methylcarbamoyl)-5-fluoro-4-oxo-3,4-dihydro-1,10-phenanthroline;
8-acetyl-3-carboxy-4-oxo-3,4-dihydro-1,10-phenanthroline;
3-carboxy-8-(N-methyl-N-{2-phenylethyl}carbamoyl)-4-oxo-3,4-dihydro-1,10-phenanthroline;
3-carboxy-8-(N-benzyl-N-isopropylcarbamoyl)-4-oxo-3,4-dihydro-1,10-phenanthroline;
3-carboxy-8-(N-benzyl-N-methylcarbamoyl)-7-hydroxy-4-oxo-3,4-dihydro-1,10-phenanthroline;
3-carboxy-8-(N-methyl-N-{4-fluorobenzyl}carbamoyl)-4-oxo-3,4-dihydro-1,10-phenanthroline;
3-carboxy-8-(N-methyl-N-{2,4-difluorobenzyl}carbamoyl)-4-oxo-3,4-dihydro-1,10-phenanthroline;
3-cyano-8-(N-benzyl-N-methylcarbamoyl)-4-oxo-3,4-dihydro-1,10-phenanthroline;
3-carboxy-8-N,Ndiethylcarbamoyl)-4-oxo-3,4-dihydro-1,10-phenanthroline; or
3-carboxy-8-(N-benzyl-N-methylcarbamoyl)-5-methyl-4-oxo-3,4-dihydro-1,10-phenanthroline; or a pharmaceutically-acceptable salt thereof, or a metabolically labile ester derivative of those compounds bearing a carboxy group or groups.

20. A compound of claim 1:
8-(N-benzyl-N-methylcarbamoyl)-5-fluoro-3-nitro-4-oxo-3,4-dihydro-1,10-phenanthroline;
8-(N-benzyl-N-methylcarbamoyl)-3 ,6-dinitro-5-methyl-4-oxo-3,4-dihydro-1,10-phenanthroline;
8-ethoxycarbonyl-3-nitro-4-oxo-3,4-dihydro-1,10-phenanthroline;
8-(N-butyl-N-ethylcarbamoyl)-3-nitro-4-oxo-3,4-dihydro-1,10-phenanthroline;
3-carboxy-6-fluoro-4-oxo-3,4-dihydro-1,10-phenanthroline;
8-(N,N-di-sec-butylcarbamoyl)-3-nitro-4-oxo-3,4-dihydro-1,10-phenanthroline;
8-(N-butyl-N-ethylcarbamoyl)-3-cyano-4-oxo-3,4-dihydro-1,10-phenanthroline;
3-carboxy-8-methoxy-4-oxo-3,4-dihydro-1,10-phenanthroline;
8-(N-cyclohexyl-N-ethylcarbamoyl)-3-nitro-4-oxo-3,4-dihydro-1,10-phenanthroline;
3-carboxy-8-(N-hexyl-N-methylcarbamoyl)-4-oxo-3,4-dihydro-1,10-phenanthroline; or
8-(N-hexyl-N-methylcarbamoyl)-3-nitro-4-oxo-3,4-dihydro-1,10-phenanthroline; or a pharmaceutically-acceptable salt thereof, or a metabolically labile ester derivative of those compounds bearing a carboxy group or groups.

21. A compound of claim 1:
6-fluoro-3-nitro-4-oxo-3,4-dihydro-1,10-phenanthroline;
3-carboxy-8-N-butyl-Nmethylcarbamoyl)-4-oxo-3,4-dihydro-1,10-phenanthroline;
3carboxy-8-(N-ethyl-N-isopropylcarbamoyl)-4-oxo-3,4-dihydro-1,10-phenanthroline;
3- carboxy-8(N-ethyl-N-propylcarbamoyl)-4-oxo-3,4-dihydro-1,10-phenanthroline;
8-(N-acetylamino)-3-carboxy-4-oxo-3,4-dihydro-1,10-phenanthroline;
3-carboxy-8-(N-{4,4,5,5,5-pentafluoropentyl}-N-methylcarbamoyl)-4-oxo-3,4-dihydro-1,10-phenanthroline;
3-carboxy-8-(N-methyl-N-ethylcarbamoyl)-7-dimethylamino-4-oxo-3,4-dihydro-1,10-phenanthroline;
3-carboxy-8-(N-tert-butoxycarbonylamino)-4-oxo-3,4-dihydro-1,10-phenanthroline;
3-carboxy-6-chloro-8-(N-butyl-N-ethylcarbamoyl)-4-oxo-3,4-dihydro-1,10-phenathroline;
8-amino-7-bromo-3-carboxy-4-oxo-3,4-dihydro-1,10-phenanthroline;
3-carboxy-8-cyano-4-oxo-3,4-dihydro-1,10-phenanthroline;
3-carboxy-8-hydroxy-4-oxo-3,4-dihydro-1,10-phenanthroline;
3-carboxy-8-carboxymethoxy-4-oxo-3,4-dihydro-1,10-phenanthroline;
8-(4-benzylpiperazin-1-ylcarbonyl)-3-nitro-4-oxo-3,4-dihydro-1,10-phenanthroline; or a pharmaceutically-acceptable salt thereof, or a metabolically labile ester derivative of those compounds bearing a carboxy group or groups.

22. A compound of claim 1:
3-[2-(2-methoxyethoxy)ethoxycarbonyl]-4-oxo-3,4-dihydro-1,10-phenanthroline;
8-(-butyl-N-ethylcarbamoyl)-3-carboxy-4-oxo-3,4-dihydro-1,10-phenanthroline;
3,6-dinitro-4-oxo-3,4-dihydro-1,10-phenanthroline;
8-carboxy-3-nitro-4-oxo-3,4-dihydro-1,10-phenanthroline;
8-(4-benzylpiperazin-1-ylcarbonyl)-3-nitro-4-oxo-3,4-dihydro-1,10-phenanthroline;
3-(2,2,2-trifluoroethylsulphonyl)-4-oxo-3,4-dihydro-1,10-phenanthroline;
8-[N-(4-fluorobenzyl)-N-methylcarbamnoyl]-3-nitro-4-oxo-3,4-dihydro-1,10-phenanthroline;
3-carboxy-8-N,Ndiethylthiocarbamoyl-4-oxo-3,4-dihydro-1,10-phenanthroline;
8-(N-benzyl-N-methylcarbamoyl)-3-cyano-5-fluoro-4-oxo-3,4-dihydro-1,10-phenanthroline;
3-acetyl-7-chloro-8-ethoxycarbony-4-oxo-3,4-dihydro-1,10-phenanthroline;
3-carboxy-5-fluoro-8-(N-2,2,3,3,4,4,4-heptafluorobutylcarbamoyl)-4-oxo-3,4-dihydro-1,10-phenanthroline;
3-carboxy-8-N-4-ethoxyphenylcarbamoyl)-4-oxo-3,4-dihydro-1,10-phenanthroline;
3-carboxy-8-carbamoyl-4-oxo-3,4-dihydro-1,10-phenanthroline;
3-carboxy-4-oxo-8-(1,2,3,4-tetrahydroisoquinolin-2-ylcarbonyl)-3,4-dihydro-1,10-phenanthroline; or
8-(N-benzyl-N-methylcarbamoyl)-7-dimethylamino-3-ethoxycarbonyl-4-oxo-3,4-dihydro-1,10-phenanthroline; or a pharmaceutically-acceptable salt thereof, or a metabolically labile ester derivative of those compounds bearing a carboxy group.

23. A pharmaceutical composition comprising one or more compounds of formula (I):

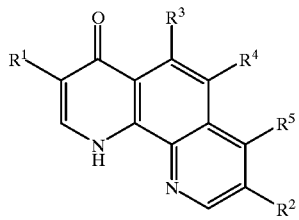

(I)

wherein R¹ is hydrogen, carboxy or a metabolically labile ester derivative thereof, cyano, halo, nitro, amino, (1–4C) alkyl, (1–4C)alkylamino, di-(1–4C)alkylamino, (1–6C) alkoxycarbonyl, (2–4C)alkanoyl, hydroxy-(1–4C)alkyl, carbamoyl, N-(1–4C)alkylcarbamoyl, (1–4C)alkylthio, (1–4C)alkylsulfinyl, (1–4C)alkylsulfonyl; phenylthio, phenylsulfinyl or phenylsulfonyl said phenyl being optionally substituted with 1 to 4 substituents selected from halo, (1–4C)alkyoxy, (1–4C)alkyl, cyano, hydroxy and trifluoromethyl; fluoro-(1–4C)alkylthio, fluoro-(1–4C) alkylsulfinyl, fluoro-(1–4C)alkylsulfonyl, (1–4C)alkoxy-(2–4C)alkoxycarbonyl, N,N-di-[(1–4C)alkyl]carbamoyl-(1–4C)alkoxycarbonyl, (1–4C)alkylamino-(2–4C) alkoxycarbonyl, di-(1–4C)alkylamino-(2–4C) alkoxycarbonyl, (1–4C)alkoxy-(2–4C)alkoxy-(2–4C) alkoxycarbonyl, (2–4C)alkanoyloxy-(1–4C)alkyl or N-[amino-(2–8C)alkyl]carbamoyl;

R²is hydrogen, hydroxy, amino, cyano, halo, (1–4C)alkyl, carboxy or a metabolically labile ester derivative thereof, (1–4C)alkylamino, di-(1–4C)alkylamino, (1–6C)alkoxycarbonyl, (2–4C)alkanoyl, (1–4C)alkoxy, carboxy-(1–4C)alkoxy, (1–4C)alkoxycarbonyl-(1–4C) alkoxy, carbamoyl, N-(1–8C)alkylcarbamoyl, N,N-di-(1–8C)alkylcarbamoyl, N-[amino-(2–8C)alkyl] carbamoyl, N-[(1–4C)alkylamino-(1–8C)alkyl] carbamoyl, N-[di-(1–4C)alkylamino-(1–8C)alkyl] carbamoyl, N-cyclohexylcarbamoyl, N-[cyclopentyl] carbamoyl, N-(1–4C)alkylcyclohexylcarbamoyl or N-(1–4C)alkylcyclopentylcarbamoyl; N-phenylcarbamoyl, N-(1–4C)alkyl-N-phenylcarbamoyl, N,N-diphenylcarbamoyl, N-[phenyl-(1–4C)alkyl]carbamoyl, N-(1–4C)alkyl-N-[phenyl-(1–4C)alkyl]carbamoyl or N,N-di-[phenyl-(1–4C)alkyl]carbamoyl said phenyl or phenyl groups being optionally substituted with 1 to 4 substituents selected from halo, (1–4C)alkyoxy, (1–4C)alkyl, cyano, hydroxy and trifluoromethyl; N-[(2–4C) alkanoyl]carbamoyl, N-[(1–4C)alkoxycarbonyl] carbamoyl, N[fluoro-(2–6C)alkyl]carbamoyl, N-[fluoro-(2–6C)alkyl]-N-(1–4C)alkylcarbamoyl or N,N-[di-fluoro-(2–6C)alkyl]carbamoyl; pyrrolidin-1-ylcarbonyl, piperidinocarbonyl, piperazin-1-ylcarbonyl or morpholinocarbonyl wherein the heterocyclic group is optionally substituted with 1 to 4 substituents selected from (1–4C)alkyl and benzyl; 1,2,3,4-tetrahydro-isoquinolin-2-ylcarbonyl, N,N-[di-(1–4C) alkyl]thiocarbamoyl, N-(2–4C)alkanoylamino or N-[(1–4)alkoxycarbonyl]amino;

R³ and R⁴, which may be the same or different, are hydrogen, (1–4C)alkyl, (2–4C)alkoxy, halo, nitro, hydroxy, fluoro-(1–4C)alkyl or pyridinyl;

or R⁴is methoxy; and

R⁵is hydrogen, hydroxy, amino, (1–4C)alkylamino, di-(1–4C)alkylamino, halo, (1–4C)alkoxy-(2–4C)alkoxy or fluoro-(1–6C)alkoxy; pyrrolidin-1-yl, piperidino, piperazin-1-yl or morpholino wherein the heterocyclic group is optionally substituted with 1 to 4 substituents selected from (1–4C)alkyl and benzyl; or a pharmaceutically-acceptable salt thereof; and a pharmaceutically-acceptable diluent or carrier.

24. A method for producing an anti-fibroproliferative effect in a host in need of such treatment, comprising administering an effective amount of a composition of claim 23.

25. The method of claim 24 wherein said said composition comprises:

3-carboxy-4-oxo-3,4dihydro-1,10-phenanthroline;

3-carboxy-5-methyl-4-oxo-3,4dihydro-1,10-phenanthroline;

3-ethoxycarbonyl-4-oxo-3,4-dihydro-1,10-phenanthroline;

3-ethoxycarbonyl-6-fluoro-4-oxo-3,4-dihydro-1,10-phenanthroline;

or a pharmaceutically acceptable salt, or a metabolically labile ester derivative thereof.

26. The method of claim 25 wherein said composition comprises 3-carboxy-4-oxo-3,4-dihydro-1,10-phenanthroline.

27. A method of treating the symptoms of a fibroproliferative disease or disorder in a host in need of such treatment comprising administering an effective amount of a composition of claim 23.

28. The method of claim 27 where the disease is rheumatoid arthritis, chronic arthritis or osteoarthritis.

29. The method of claim 27 wherein the disease is hepatic cirrhosis.

30. The method of claim 27 where the disease is pulmonary fibrosis, renal fibrosis, cardiac fibrosis, arteriosclerosis or tumor associated fibrosis.

31. A method of treating scar tissue formation following injury or surgery in a host in need of such treatment comprising adminstering an effective amount of a composition of claim 23.

* * * * *